(12) United States Patent
Bermudes

(10) Patent No.: US 10,626,403 B2
(45) Date of Patent: Apr. 21, 2020

(54) LIVE BACTERIAL VECTORS FOR PROPHYLAXIS OR TREATMENT

(71) Applicant: David Gordon Bermudes, Woodland Hills, CA (US)

(72) Inventor: David Gordon Bermudes, Woodland Hills, CA (US)

(73) Assignee: Aviex Textnologies LLC, New York, NY (US)

( * ) Notice: Subject to any disclaimer, the term of this patent is extended or adjusted under 35 U.S.C. 154(b) by 0 days.

(21) Appl. No.: 16/148,055

(22) Filed: Oct. 1, 2018

(65) Prior Publication Data

US 2019/0017057 A1 Jan. 17, 2019

Related U.S. Application Data

(60) Division of application No. 15/131,083, filed on Apr. 18, 2016, now Pat. No. 10,087,451, which is a
(Continued)

(51) Int. Cl.
*C12N 15/74* (2006.01)
*A61K 39/12* (2006.01)
(Continued)

(52) U.S. Cl.
CPC .............. *C12N 15/74* (2013.01); *A61K 39/12* (2013.01); *A61K 39/145* (2013.01); *C12N 1/36* (2013.01);
(Continued)

(58) Field of Classification Search
CPC ............ A61K 39/145; A61K 2039/522; A61K 2039/523; A61K 2039/542; A61K 2039/552; A61K 39/12; C12N 2760/16134; C12N 9/2402; C12N 15/74; C12N 1/36; C12Y 302/01018
See application file for complete search history.

(56) References Cited

U.S. PATENT DOCUMENTS

2003/0113293 A1* 6/2003 Bermudes .............. A61K 48/00
424/93.2

OTHER PUBLICATIONS

Murray et al., ( J. Bacteriol. Dec. 2004 186(24):8516-8523). (Year: 2004).*

* cited by examiner

*Primary Examiner* — Jana A Hines
(74) *Attorney, Agent, or Firm* — Tully Rinckey PLLC; Steven M. Hoffberg

(57) ABSTRACT

A live bacterium, having a DNA construct stabilized against transduction of other bacteria, having a promoter sequence and encoding a fusion peptide, comprising a bacterial secretion peptide portion and a non-bacterial immunogenic polypeptide portion, having a nucleotide sequence coding for the non-bacterial immunogenic polypeptide portion which has at least one codon optimized for bacterial expression. The bacterium has a secretion mechanism which interacts with at least the bacterial secretion peptide portion to cause a secretion of the fusion peptide from the bacterium, and a genetic virulence attenuating mutation. The bacterium is adapted to act as an animal vaccine, to transiently infect a tissue of the animal, and cause an immunity response to the non-bacterial immunogenic polypeptide portion in the animal to a non-bacterial organism associated with the non-bacterial immunogenic polypeptide portion.

20 Claims, 8 Drawing Sheets

Specification includes a Sequence Listing.

Related U.S. Application Data division of application No. 13/892,380, filed on May 13, 2013, now Pat. No. 9,315,817, which is a continuation of application No. 13/369,333, filed on Feb. 9, 2012, now Pat. No. 8,440,207, which is a continuation of application No. 11/859,569, filed on Sep. 21, 2007, now abandoned.

(60) Provisional application No. 60/826,542, filed on Sep. 22, 2006.

(51) Int. Cl.
*A61K 39/145* (2006.01)
*C12N 1/36* (2006.01)
*C12N 9/24* (2006.01)
*A61K 39/00* (2006.01)

(52) U.S. Cl.
CPC .... *C12N 9/2402* (2013.01); *C12Y 302/01018* (2013.01); *A61K 2039/522* (2013.01); *A61K 2039/523* (2013.01); *A61K 2039/542* (2013.01); *A61K 2039/552* (2013.01); *C12N 2760/16134* (2013.01)

Fig. 5

ClyA:Antigen Fusion Expression Plasmid

Labels: EcoRV, NcoI, Ptrc, ClyA:Antigen, HindIII, T1 T2, NotI/PacI, bla, SphI

Fig. 6

Antigen:Autotrans-Porter Fusion Expression Plasmid

Labels: EcoRV, NcoI, Ptrc, S, Antigen (H5), translocator, HindIII, T1 T2, NotI/PacI, bla, SphI Spontaneous recombination

Bacterial chromosome lacking 17.7 IS200

Bacterial chromosome containing both IS200s

LIVE BACTERIAL VECTORS FOR PROPHYLAXIS OR TREATMENT

CROSS REFERENCE TO RELATED APPLICATIONS

The present applcation is a Division of U.S. patent application Ser. No. 15/131,083, filed Apr. 18, 2016, now U.S. Pat. No. 10,087,451, issued Oct. 2, 2018, which is a Division of U.S. patent application Ser. No. 13/892,380, filed May 13, 2013, now U.S. Pat. No. 9,315,817, issued Apr. 19, 2016, which is a Continuation of U.S. patent application Ser. No. 13/369,333, filed Feb. 9, 2012, now U.S. Pat. No. 8,440,207, issued May 14, 2013, which is a Continuation of U.S. patent application Ser. No. 11/859,569, filed Sep. 21, 2007, now abandoned, which Claims benefit of priority from U.S. Provisional Patent Application 60/826,542, filed Sep. 22, 2006, each of which is expressly incorporated herein by reference.

FIELD OF THE INVENTION

This invention is generally in the field of live bacterial vaccines for viral infection prophylaxis or treatment.

BACKGROUND OF THE INVENTION

Citation or identification of any reference herein, or any section of this application shall not be construed as an admission that such reference is available as prior art to the present application.

There are three types of *influenza* viruses *Influenza* A, B, and C. *Influenza* types A or B viruses cause epidemics of disease almost every winter. In the United States, these winter *influenza* epidemics can cause illness in 10% to 20% of people and are associated with an average of 36,000 deaths and 114,000 hospitalizations per year. *Influenza* type C infections cause a mild respiratory illness and are not thought to cause epidemics. *Influenza* type A viruses are divided into subtypes based on two proteins on the surface of the virus. These proteins are termed hemagglutinin (H) and neuraminidase (N). *Influenza* A viruses are divided into subtypes based on these two proteins. There are 16 different hemagglutinin subtypes H1, H2, H3, H4, H6, H7, H8, H9 H10 H11 H12, H13, H14, H15 or H16 and 9 different neuraminidase subtypes N1 N2 N3 N4 N5 N6 N7 N8 or N9, all of which have been found among *influenza* A viruses in wild birds. Wild birds are the primary natural reservoir for all subtypes of *influenza* A viruses and are thought to be the source of *influenza* A viruses in all other animals. The current subtypes of *influenza* A viruses found in people are A(H1N1) and A(H3N2). *Influenza* B virus is not divided into subtypes.

In 1918, a new highly pathogenic *influenza* H1N1 pandemic swept the world, killing an estimated 20 and 50 million people. The H1N1 subtype circulated from 1918 until 1957 which then was replaced by viruses of the H2N2 subtype, which continued to circulate until 1968. Since 1968, H3N2 viruses have been found in the population. Because H1N1 viruses returned in 1977, two *influenza* A viruses are presently co-circulating (Palese and Garcia-Sarstre J Clin Invest, July 2002, Volume 110, Number 1, 9-13). The pathogenicity of the initial 1918 H1N1 has not been equaled by any of the latter H1N1, H2N2 or H3N2 subtypes, although infection from some subtypes can be severe and result in death. By molecular reconstruction, the genome of the 1918 flu including the amino acid sequences of the H1 and N1 antigens is now known (Kaiser, Science 310: 28-29, 2005; Tumpey et al., Science 310: 77-81, 2005).

In 1997, 2003, and again in 2004, antigenically-distinct avian H5N1 *influenza* viruses emerged as pandemic threats to human beings. During each of these outbreaks there was concern that the avian viruses would adapt to become transmissible from human to human. Furthermore, oseltamivir (Tamiflu®) was ineffective in 50% of avian *influenza* patients in Thailand (Tran et al. N. Engl. J. Med 350: 1179, 2004) and a new mutation in the neuraminidase has been identified which causes resistance to oseltamivir. Sequence analysis of the neuraminidase gene revealed the substitution of tyrosine for histidine at amino acid position 274 (H274Y), associated with high-level resistance to oseltamivir in *influenza* (N1) viruses (Gubareva et al., Selection of *influenza* virus mutants in experimentally infected volunteers treated with oseltamivir. J Infect Dis 2001; 183:523-531; de Jong et al., Oseltamivir Resistance during Treatment of *Influenza* A (H5N1) Infection. N. Engl. J. Med. 353:2667-2672, 2005). Such changes may alter the antigenic nature of the protein and reduce the effectiveness of vaccines not matched to the new variant. Other avian *influenza* strains of potential danger include H1N1, H7N7 and H9N2.

The optimum way of dealing with a human pandemic virus would be to provide a clinically approved well-matched vaccine (i.e., containing the hemagglutinin and/or neuraminidase antigens of the emerging human pandemic strain), but this cannot easily be achieved on an adequate timescale because of the time consuming method of conventional *influenza* vaccine production in chicken eggs.

2.1 Live Bacterial Vaccine Vectors

Live attenuated bacterial vaccine vectors offer an important alternative to conventional chicken egg based vaccines. Growth on embryonated hen eggs, followed by purification of viruses from allantoic fluid, is the method by which *influenza* virus has traditionally been grown for vaccine production. More recently, viruses have been grown on cultured cell lines, which avoids the need to prepare virus strains that are adapted to growth on eggs and avoids contamination of the final vaccine with egg proteins. However, because some of the vaccine virus may be produced in canine tumor cells (e.g., MDCK), there is concern for contamination of the vaccine by cancer causing elements. Moreover, both must undergo a labor intensive and technically challenging purification process, with a total production time of 3 to 6 months. Because of the time factors and scale-up, these vaccines are produced in large, but finite batches. Meeting a world-wide demand requires stockpiling of multiple batches. Therefore, traditionally produced vaccine produced before a pandemic, would likely be generated based upon an avian *influenza* virus and its antigens more than a year earlier and therefore may not be well matched to an emerging variant and could result in only partial protection. Bacterial vectors self replicate in simple growth media can be produced extremely rapidly by virtue of exponential growth and require minimal purification such as a single centrifugation and resuspension in a pharmaceutically acceptable excipient.

Human studies have shown that antibody titers against hemagglutinin of human *influenza* virus are correlated with protection (a serum sample hemagglutination-inhibition titer of about 30-40 gives around 50% protection from infection by a homologous virus) (Potter & Oxford (1979) Br Med Bull 35: 69-75). Antibody responses are typically measured by enzyme linked immunosorbent assay (ELISA), immunoblotting, hemagglutination inhibition, by microneutralisation, by single radial immunodiffusion (SRID), and/or by single radial hemolysis (SRH). These assay techniques are well known in the art.

Salmonella bacteria have been recognized as being particularly useful as live "host" vectors for orally administered vaccines because these bacteria are enteric organisms that, when ingested, can infect and persist in the gut (especially the intestines) of humans and animals.

As a variety of Salmonella bacteria are known to be highly virulent to most hosts, e.g., causing typhoid fever or severe diarrhea in humans and other mammals, the virulence of Salmonella bacterial strains toward an individual that is targeted to receive a vaccine composition must be attenuated. Attenuation of virulence of a bacterium is not restricted to the elimination or inhibition of any particular mechanism and may be obtained by mutation of one or more genes in the Salmonella genome (which may include chromosomal and non-chromosomal genetic material). Thus, an "attenuating mutation" may comprise a single site mutation or multiple mutations that may together provide a phenotype of attenuated virulence toward a particular host individual who is to receive a live vaccine composition for Avian Influenza. In recent years, a variety of bacteria and, particularly, serovars of Salmonella enterica, have been developed that are attenuated for pathogenic virulence in an individual (e.g., humans or other mammals), and thus proposed as useful for developing various live bacterial vaccines (see, e.g., U.S. Pat. Nos. 5,389,368; 5,468,485; 5,387,744; 5,424,065; Zhang-Barber et al., Vaccine, 17; 2538-2545 (1999); all expressly incorporated herein by reference). In the case of strains of Salmonella, mutations at a number of genetic loci have been shown to attenuate virulence including, but not limited to, the genetic loci phoP, phoQ, cdt, cya, crp, poxA, rpoS, htrA, nuoG, pmi, pabA, pts, damA, purA, purB, purI, zwf, aroA, aroC, gua, cadA, rfc, rjb, rfa, ompR, msbB and combinations thereof.

Bacterial flagella are known to be antigenic and subject to antigenic or phase variation which is believed to help a small portion of the bacteria in escaping the host immune response. The bacterial flagellar antigens are referred to as the H1 and H2 antigens. To avoid confusion with the viral hemagglutinin H antigen, the bacterial flagellar H antigen will be referred to as fH henceforth. Because the Salmonella-based vaccination of a heterologous antigen is dependent upon the bacteria's ability to colonize the gut, which may be reduced do to the initial immune response, the vaccination ability of the second immunization may be diminished due to an immune response to the vector. In Salmonella, Hin invertase belongs to the recombinase family, which includes Gin invertase from phage Mu, Cin invertase from phage P1, and resolvases from Tn3 and the transposon (Glasgow et al. 1989, p. 637-659. In, D. E. Berg, and M. M. Howe (ed.), Mobile DNA. American Society for Microbiology, Washington, D.C.). Hin promotes the inversion of a chromosomal DNA segment of 996 bp that is flanked by the 26-bp DNA sequences of hixL and hixR (Johnson and Simon. 1985. Cell 41:781-791). Hin-mediated DNA inversion in S. typhimurium leads to the alternative expression of the fH1 and fH2 flagellin genes known as phase variation. Hin (21 kDa) exists in solution as a homodimer and binds to hix sites as a dimer (Glasgow et al. 1989. J. Biol. Chem. 264:10072-10082). In addition to Hin and the two hix sites, a cis-acting DNA sequence (recombinational enhancer) and its binding protein (Fis, 11 kDa) are required for efficient inversion in vitro (Johnson et al. 1986. Cell 46:531-539). Live Salmonella vaccines have not had deletions of the Hin gene nor defined fH1 or fH2 antigens, nor have they been constructed such that they lack fH antigens altogether. Accordingly, live Salmonella vaccines have not been constructed to maximize a prime-boost strategy which alternates or eliminates the fH antigen whereby the immune response of the fH antigen of the first immunization (prime) is not specific for the antigen of the second immunization (boost). Therefore, the boost immunization is not diminished by a rapid elimination by the immune system, and is therefore able to persist longer and more effectively present the immunizing antigen.

Introduction of viral genes into bacteria results in genetically engineered microorganisms (GEMs) for which there may be concern regarding containment of the introduced gene in the environment and its ability to reassort. Such genes could in theory provide virulence factors to non-pathogenic or less pathogenic viral strains if allowed to recombine under circumstances were the bacterial vaccine could co-occur at the same time in the same individual as a wild type viral infection. Thus, methods that reduce bacterial recombination and increase bacterial genetic isolation are desirable.

Insertion sequences (IS) are genetic elements that can insert copies of themselves into different sites in a genome. These elements can also mediate various chromosomal rearrangements, including inversions, deletions and fusion of circular DNA segments and alter the expression of adjacent genes. IS200 elements are found in most Salmonella species. S. typhimurium strain LT2 has six IS200s. Salmonella typhimurium strain 14028 has been described to possess an additional IS200 element at centisome 17.7 which is absent in other commonly studied Salmonella strains LT2 and SL1344 (Murray et al., 2004 Journal of Bacteriology, 186: 8516-8523). These authors describe a spontaneous hot spot (high frequency) deletion of the Cs 17.7 to Cs 19.9 region. Live Salmonella vaccines have not had deletions of IS200 elements which would limit such recombination events.

Salmonella strains are known to possess phage and prophage elements. Such phage are often capable of excision and infection of other susceptible strains and are further capable of transferring genes from one strain by a process known as transduction. Live Salmonella vaccines have not had deletions in phage elements such as phage recombinases which exist in Salmonella, such that the phage are no longer capable of excision and reinfection of other susceptible strains.

Salmonella strains are known to be capable of being infected by bacteria phage. Such phage have the potential to carry genetic elements from one Salmonella strain to another. Live Salmonella vaccines have not comprised mechanisms to limit phage infection such as the implantation and constitutive expression of the P22 phage repressor C2.

Bacterial expression of the viral hemagglutinin genes was first described by Heiland and Gething (Nature 292: 581-582, 1981) and Davis et al., (Proc. Natl. Acad. Sci. USA 78: 5376-5380). These authors suggest that the recombinant protein could be used as a vaccine without regard to the fact that the viral genetic loci are not optimal for bacterial expression. These authors did not suggest the use of live bacterial vectors as vaccine carriers, such as the genetically stabilized and isolated vectors of the present application, nor the use of defined flagellar antigens or no flagellar antigens. Nor did these authors suggest the use of secreted proteins.

Use of secreted proteins in live bacterial vectors has been demonstrated by several authors. Holland et al. (U.S. Pat. No. 5,143,830, expressly incorporated herein by reference)

have illustrated the use of fusions with the C-terminal portion of the hemolysin A (hlyA) gene. When co-expressed in the presence of the hemolysin protein secretion channel (hlyBD), heterologous fusions are readily secreted from the bacteria. Similarly, Galen et al. (Infection and Immunity 2004 72: 7096-7106) have shown that heterologous fusions to the ClyA are secreted and immunogenic. Other heterologous protein secretion systems include the use of the autotransporter family. For example, Veiga et al. (2003 Journal of Bacteriology 185: 5585-5590) demonstrated hybrid proteins containing the b-autotransporter domain of the immunoglogulin A (IgA) protease of *Nisseria gonorrhoea*.

Bacterial expression of the viral hemagglutinin genes was first described by Heiland and Gething (Nature 292: 581-582, 1981) and Davis et al., (Proc. Natl. Acad. Sci. USA 78: 5376-5380). These authors teach that the antigens may be purified from the bacteria in order to be used as vaccines and did not suggest the use of live attenuated bacterial vectors. Furthermore, the codon usage of the viral genome is not optimal for bacterial expression. Accordingly, a gram-negative bacterium of the enterobacteraceae such as *E. coli* and *Salmonella* will have a different codon usage preference (National Library of Medicine, National Center for Biotechnology Information, GenBank Release 150.0 [Nov. 25, 2005]) and would not be codon optimized. Further, these authors used antibiotic-containing plasmids and did not use stable chromosomal localization. Nor did these authors suggest heterologous fusions in order for the bacteria to secrete the antigens.

Kahn et al. (EP No. 0863211) have suggested use of a live bacterial vaccine with in vivo induction using the *E. coli* nitrite reductase promoter nirB. These authors further suggest that the antigenic determinant may be an antigenic sequence derived from a virus, including *Influenza* virus. However, Khan et al. did not describe a vaccine for avian *influenza* virus. They did not describe the appropriate antigens for an Avian *Influenza* virus, the hemagglutinin and neuraminidase, and did not describe how to genetically match an emerging Avian *Influenza* virus. Furthermore, it has become apparent that certain assumptions, and experimental designs described by Khan et al. regarding live Avian *Influenza* vaccines would not be genetically isolated or have improved genetic stability in order to provide a live vaccine for Avian *Influenza* that would be acceptable for use in humans. For example, Khan et al. state that any of a variety of known strains of bacteria that have an attenuated virulence may be genetically engineered and employed as live bacterial carriers (bacterial vectors) that express antigen polypeptides to elicit an immune response including attenuated strains of *S. typhimurium* and, for use in humans, attenuated strains of *S. typhi* (i.e., *S. enterica* serovar *Typhi*). In support of such broad teaching, they point to the importance of "non-reverting" mutations, especially deletion mutations which provide the attenuation. However, non-reversion only refers to the particular gene mutated, and not to the genome per se with its variety of IS200, phage and prophage elements capable of a variety of genetic recombinations and/or even transductions to other bacterial strains. Khan et al. did not describe a bacterial strain with improved genetic stability, nor methods to reduce genetic recombination, such as deletion of the IS200 elements. Khan et al. did not describe a bacterial strain with improved genetic stability by deletion of the bacteria phage and prophage elements nor limiting their transducing capacity. Neither did Khan et al. describe methods to minimize bacterial genetic exchange, such as constitutive expression of the P22 C2 phage repressor.

The above comments illustrate that Khan et al. have not provided the field with an effective vaccine against avian *influenza*. Clearly, needs remain for a genetically isolated and genetically stable, orally administered vaccine against Avian *Influenza* which is capable of rapid genetically matching an emerging pathogenic variant.

SUMMARY OF THE INVENTION

The present invention provides live attenuated bacterial strains that express one or more immunogenic polypeptide antigens of a virus, preferably an Avian *Influenza* virus, that is effective in raising an immune response in mammals.

In particular, one aspect of the invention relates to live attenuated bacterial strains which may include *Salmonella* vectoring avian *influenza* antigens that can be administered orally to an individual to elicit an immune response to protect the individual from Avian *Influenza*.

The preferred bacteria are serovars of *Salmonella*. Preferably, the bacteria are genetically isolated from infecting bacteria phage and have improved genetic stability by virtue of deletion of IS200 and phage elements. The preferred *Salmonella* strains of the invention are attenuated by mutations at genetic loci which, alone or in combination, provides sufficient attenuation, and defined flagellar antigens for an improved prime/boost strategy. The attenuating mutations may be those of strains known to exhibit a degree of safety in humans including but not limited to Ty21a, CMV906, CMV908, CMV906-htr, CMV908-htr, Ty800, holavax, MO1ZH09 or VNP20009 or may be novel combinations of mutations.

Whereas the current medical practice uses derivatives of pathogenic avian strains in chicken eggs to provide vaccines that generate an immune response including antibodies in humans or other mammals against known pathogenic avian strains, the invention provides methods and compositions comprising genetically isolated bacterial vectors with enhanced genetic stability vectoring Avian *Influenza* virus antigens to protect against emerging pathogenic human strains.

Furthermore, whereas the prior art often fails to achieving close antigenic match between the vaccine strain and the target strain, the invention targets viruses for vaccine strains based on their emerging pathogenicity, and produces an effective vaccine more closely matched to the antigen profile of the emerging pathogen. As the invention requires detailed knowledge of the antigenic profile of an emerging strain, such a vaccine can be produced at the time of need in order to reduce the risk of an unmatched vaccine and potential effects of partial protection in a human pandemic outbreak. Thus the invention provides vaccines for protecting a human patient against infection by an emerging Avian *Influenza* virus strain.

Preferably, the vaccines according to the present invention comprise genetically stable bacterial vectors carrying one or more antigen from an Avian *Influenza* virus strain that can cause highly pathogenic Avian *Influenza*.

The invention further preferably provides for vaccines against oseltamivir resistant strains.

Accordingly, when orally administered to an individual, a live *Salmonella* bacterial vaccine, in accordance with the present invention, that is genetically engineered to express one or more Avian *Influenza* antigens as described herein have the inherent ability to establish a population (infection) in the gut and, if properly modified they could provide a desirable source of immunogenic Avian *Influenza* antigen polypeptide(s) to elicit an immune response in the mucosal tissue of the individual.

The antigen(s) can invoke an antibody response in the patient that is capable of neutralizing the emerging avian *influenza* vaccine strains with high efficiency, as well as emerging heterologous Avian *Influenza* vaccine strains, with moderate efficiency. Preferably, the emerging avian *influenza* vaccine will be within the same hemagglutinin and or neuraminidase type (i.e., H1, H5, H5 (H274Y), H7 or H9 and/or N1, N2 or N7) as are the current pathogenic avian *influenza* strains.

The live vaccine compositions are suitable for oral administration to an individual to provide protection from avian *influenza*. Preferably, a vaccine composition comprises a suspension of a live bacterial strain described herein in a physiologically accepted buffer or saline solution that can be swallowed from the mouth of an individual. However, oral administration of a vaccine composition to an individual may also include, without limitation, administering a suspension of a bacterial vaccine strain described herein through a nasojejunal or gastrostomy tube and administration of a suppository that releases a live bacterial vaccine strain to the lower intestinal tract of an individual. Vaccines of the invention may be formulated for delivery by other various routes e.g. by intramuscular injection, subcutaneous delivery, by intranasal delivery (e.g. WO00/47222, U.S. Pat. No. 6,635,246), intradermal delivery (e.g. WO02/074336, WO02/067983, WO02/087494, WO02/0832149 WO04/016281) by transdermal delivery, by transcutaneous delivery, by topical routes, etc. Injection may involve a needle (including a microneedle), or may be needle-free.

Annual human *Influenza* vaccines typically include more than one *Influenza* strain, with trivalent vaccines being normal (e.g. two *Influenza A* virus antigens, and one *Influenza B* virus antigen). In pandemic years, however, a single monovalent strain may be used. Thus the pathogenic avian antigen(s) described above may be the sole *Influenza* antigen(s) in a vaccine of the invention, or the vaccine may additionally comprise antigen(s) from one or more (e.g. 1, 2, 3, 4 or more) annual *Influenza* virus strains. Specific vaccines of the invention thus include: (i) a vaccine comprising the pathogenic avian antigen(s) as the sole *Influenza* antigen(s); (ii) a vaccine comprising the pathogenic avian antigen(s) plus antigen(s) from another pathogenic Avian *Influenza* strain (e.g., H1N1, H5N1, H7N7, H2N9, H9N2).

Vaccines of the invention use one or more avian antigens to protect patients against infection by an *Influenza* virus strain that is capable of human-to-human transmission i.e. a strain that will spread geometrically or exponentially within a given human population without necessarily requiring physical contact. The patient may also be protected against strains that infect and cause disease in humans, but that are caught from birds rather than from other humans (i.e., bird to human transmission). The invention is particularly useful for protecting against infection by pandemic, emerging pandemic and future pandering human strains e.g. for protecting against H5 and N1 *influenza* subtypes. Depending on the particular season and on the nature of the antigen included in the vaccine, however, the invention may protect against any hemagglutinin subtypes, including H1, H2, H3, H4, H5, H6, H7, H8, H9, H10, H11, H12, H13, H14, H15 or H16 or various neuraminidase subtypes, including N1, N2, N3, N4, N5, N6, N7, N8 or N9.

The characteristics of an *Influenza* strain that give it the potential to cause a pandemic outbreak may include: (a) it contains a new or antigenically altered hemagglutinin compared to the hemagglutinins in currently-circulating human strains i.e., one that has not been evident in the human population for over a decade (e.g. H2), or has not previously been seen at all in the human population (e.g. H5, H6 or H9, that have generally been found only in bird populations), such that the human population will be immunologically naive to the strain's hemagglutinin or that is a subtype which is antigenically altered by changes in amino acid sequence or glycosylation; (b) it is capable of being transmitted horizontally in the human population; (c) is capable of being transmitted from animals (including birds, dogs, pigs) to humans; and/or (d) it is pathogenic to humans.

As a preferred embodiment of the invention protects against a strain that is capable of human-to-human or bird-to-human or bird-to-bird transmission, one embodiment of the invention in accordance with that aspect will generally include at least one gene that originated in a mammalian (e.g. in a human) *Influenza* virus and one gene which originated in a bird or non-human vertebrate. Vaccines in accordance with various aspects of the invention may therefore include an antigen from an Avian *Influenza* virus strain. This strain is typically one that is capable of causing highly pathogenic Avian *Influenza* (HPAI). HPAI is a well-defined condition (Alexander Avian Dis (2003) 47(3 Suppl):976-81) that is characterized by sudden onset, severe illness and rapid death of affected birds/flocks, with a mortality rate that can approach 100%. Low pathogenicity (LPAI) and high pathogenicity strains are easily distinguished e.g. van der Goot et al. (Epidemiol Infect (2003) 131(2):1003-13) presented a comparative study of the transmission characteristics of low and high pathogenicity H5N2 avian strains. For the 2004 season, examples of HPAI strains are H5N1 *Influenza* A viruses e.g. A/Viet Nam/I 196/04 strain (also known as A Vietnam/3028/2004 or A/Vietnam/3028/04). The skilled person will thus be able to identify or predict future HPAI strains and the DNA sequence and amino acid compositions of the H and N antigens as and when they emerge. The Avian *Influenza* strain may be of any suitable hemagglutinin subtype, including H1, H2, H3, H4, H5, H6, H7, H8, H9, H10, H11, H12, H13, H14, H15 or H16. The Avian *Influenza* strain may further be of any suitable neuraminidase subtype N1, N2, N3, N4, N5, N6, N7, N8, or N9. The vaccines of the invention may comprise two or more (i.e., two, three, four, or five) Avian *Influenza* hemagglutinin and neuraminidase antigens. Such Avian *Influenza* strains may comprise the same or different hemagglutinin subtypes and the same or different neuraminidase subtypes.

A preferred vaccine composition will contain a sufficient amount of live bacteria expressing the antigen(s) to produce an immunological response in the patient. Accordingly, the attenuated *Salmonella* strains described herein are both safe and useful as live bacterial vaccines that can be orally administered to an individual to provide immunity to Avian *Influenza* and, thereby, protection from Avian *Influenza*.

Although not wishing to be bound by any particular mechanism, an effective mucosal immune response to Avian *Influenza* antigen(s) in humans by oral administration of genetically engineered, attenuated strains of *Salmonella* strains as described herein may be due to the ability of such mutant strains to persist in the intestinal tract. Each bacterial strain useful in the invention carries an antigen-expressing plasmid or chromosomally integrated cassette that encodes and directs expression of one or more Avian *Influenza* antigens of Avian *Influenza* virus when resident in an attenuated *Salmonella* strain described herein. As noted above, Avian *Influenza* antigens that are particularly useful in the invention include an H1, H5, H5 (H274Y), H7 or H9 antigen polypeptide (or immunogenic portion thereof), a N1, N2 or N7 antigen polypeptide (or immunogenic portion thereof), and a fusion polypeptide comprising a heterologous secretion peptide linked in-frame to the antigenic peptide.

The serovars of *S. enterica* that may be used as the attenuated bacterium of the live vaccine compositions described herein include, without limitation, *Salmonella enterica* serovar *Typhimurium* (*S. typhimurium*), *Salmonella montevideo*, *Salmonella enterica* serovar *Typhi* (*S. typhi*), *Salmonella enterica* serovar *Paratyphi B* (*S. paratyphi* 13), *Salmonella enterica* serovar *Paratyphi C* (*S. paratyphi C*), *Salmonella enterica* serovar *Hadar* (*S. hadar*), *Salmonella enterica* serovar *Enteriditis* (*S. enteriditis*), *Salmonella enterica* serovar *Kentucky* (*S. kentucky*), *Salmonella enterica* serovar *Infantis* (*S. infantis*), *Salmonella enterica* serovar *Pullorurn* (*S. pullorum*), *Salmonella enterica* serovar *Gallinarum* (*S. gallinarum*), *Salmonella enterica* serovar *Muenchen* (*S. muenchen*), *Salmonella enterica* serovar *Anaturn* (*S. anatum*), *Salmonella enterica* serovar *Dublin* (*S. dublin*), *Salmonella enterica* serovar *Derby* (*S. derby*), *Salmonella enterica* serovar *Choleraesuis* var. *kunzendorf* (*S. cholerae kunzendorf*), and *Salmonella enterica* serovar *minnesota* (*S. minnesota*).

By way of example, live Avian *Influenza* vaccines in accordance with aspects of the invention include known strains of *S. enterica* serovar *Typhimurium* (*S. typhimurium*) and *S. enterica* serovar *Typhi* (*S. typhi*) which are further modified as provided by the invention to form suitable vaccines for the prevention and treatment of Avian *Influenza*. Such Strains include Ty21a, CMV906, CMV908, CMV906-htr, CMV908-htr, Ty800, aroA-/serC-, holavax, M01ZH09, VNP20009.

Novel strains are also encompassed that are attenuated in virulence by mutations in a variety of metabolic and structural genes. The invention therefore may provide a live vaccine composition for protecting against Avian *Influenza* comprising a live attenuated bacterium that is a serovar of *Salmonella enterica* comprising, an attenuating mutation in a genetic locus of the chromosome of said bacterium that attenuates virulence of said bacterium and wherein said attenuating mutation is the Suwwan deletion (Murray et al., 2004) or combinations with other known attenuating mutations. Other attenuating mutation useful in the *Salmonella* bacterial strains described herein may be in a genetic locus selected from the group consisting of phoP, phoQ, edt, cya, crp, poxA, rpoS, htrA, nuoG, pmi, pabA, pts, damA, purA, purB, purI, zwf, purF, aroA, aroB, aroC, aroD, serC, gua, cadA, rfc, rjb, rfa, ompR, msbB and combinations thereof.

The invention may also provide a process for preparing genetically stable bacterial vaccines for protecting a human patient against infection by an Avian *Influenza* virus strain, comprising genetically engineering the avian antigen from an Avian *Influenza* virus strain that can cause highly pathogenic Avian *Influenza* to comprise a bacterially codon optimized expression sequence within a bacterial plasmid expression vector or chromosomal localization expression vector and further containing engineered restriction endonuclease sites such that the bacterially codon optimized expression gene contains subcomponents which are easily and rapidly exchangeable in order to facilitate rapid exchange of the genetic subcomponents to achieve a well matched antigen to the emerging Avian *Influenza* pathogen. The plasmid and/or chromosomal expression constructs may be further modified to result in the secretion of the viral antigens. Administration of the vaccine to the patient invokes an antibody response that is capable of neutralizing said Avian *Influenza* virus strain.

The invention may also provide methods and compositions for producing a bacterial vector expressing one or more Avian *Influenza* antigens where said bacterial vector has one or more deletions in IS200 elements which results in enhance genetic stability. The composition and methods comprise a bacterial strain with a deletion in the IS200 elements, such that the bacteria are no longer capable of genetic rearrangement using IS200 elements. Such a deletion is generated in any one or more IS200 element, which is then confirmed using standard genetic techniques.

The invention may also provide methods and compositions for producing a genetically stabilized bacterial vector expressing one or more Avian *Influenza* antigens where said bacterial vector has one or more deletions in bacteria phage or prophage elements which enhanced genetic stability and prevent phage excision. The composition and methods comprise a bacterial strain with one or more deletions in bacteria phage or prophage elements, such that the bacteria are no longer capable of genetic rearrangement using bacteria phage or prophage elements. Such a deletion is generated in any bacteria phage or prophage elements, which is then confirmed using standard genetic techniques. Such strains have phage with reduced capacity for transduction of genes to other strains.

The invention may also provide methods and compositions for producing a bacterial vector expressing one or more avian *influenza* antigens where said bacterial vector constitutively expresses the P22 phage C2 repressor, thereby preventing new infections by bacteria phage and further preventing subsequent phage transductions by these phage.

Live *Salmonella* vaccines have not had deletions of the Hin gene nor defined fH1 or fH2 antigens, nor have they been constructed such that they lack fH antigens altogether. Accordingly, prior live *Salmonella* vaccines have not been constructed to maximize a prime-boost strategy which alternates or eliminates the fH antigen whereby the immune response of the fH antigen of the first immunization (prime) is not specific for the antigen of the second immunization (boost). Therefore, the boost immunization is not diminished by a rapid elimination by the immune system, and is therefore able to persist longer and more effectively present the immunizing heterologous Avian *Influenza* antigen.

An embodiment of the present invention therefore may also provide methods and compositions for producing a bacterial vector expressing one or more Avian *Influenza* antigens where said bacterial vector has a defined flagellar H antigen (fH). The composition and methods comprise a bacterial strain with a deletion in the Hin recombinase gene, such that the bacteria are no longer capable of alternating between fH1 and fH2 antigens. Such a deletion is generated in either an fH1 or fH2 serologically defined strain, which is then reconfirmed following deletion or disruption of the Hin recombinase gene. The invention further provides methods and compositions for producing a bacterial vector which lacks flagellar antigens generated by deletion of the fliBC genes (i.e., fH0). Therefore, an improved composition for a prime/boost strategy is provided where the second vaccination comprises administration of a vaccine where the fH antigen composition is different from the first vaccination.

The invention may also provide a method for protecting a human patient against infection by an Avian *Influenza* virus strain with an improved prime/boost strategy, comprising the step of administering to the patient a vaccine that comprises an antigen from an Avian *Influenza* virus strain that can cause highly pathogenic Avian *Influenza* or 1918

*influenza* within a bacterial vector expressing one or more Avian *Influenza* antigens where said bacterial vector has a defined fH antigen or no fH antigen (i.e., fH1, fH2, or fH0). The invention may further provide a method of administering a second bacterial vector expressing one or more Avian *Influenza* antigens comprising a second step where the second administration where said bacterial vector has a defined fH antigen which is different fH antigen composition than the fH antigen of the first administration or no fH antigen. The second administration includes a bacterial vaccine where the first vaccine administration is a bacterial vaccine of the present invention or is another vaccine not encompassed by the present application, e.g., another bacterial vaccine or an egg-based vaccine.

Similarly, the invention may also provide a kit comprising (a) a first container comprising a bacterial expression codon optimized antigen from a pathogenic Avian *Influenza* virus strain containing unique genetically engineered restriction sites contained within either a bacterial protein expression plasmid or a bacterial chromosomal protein expression vector and (b) a second container comprising bacterial vector(s) with one or more (e.g., fH1, fH2 or fH0) flagellar antigen(s). Component (a) will be modifiable to genetically match an emerging Avian *Influenza* virus using standard in vitro molecular techniques and can be combined with component (b) to generate one or more bacterial strains with defined flagellar antigens which constitute a live vaccine. The variation(s) in flagellar antigens provided by the kit provide for more than one live vaccine strain in which a first immunization (prime) using one strain may be followed at an appropriate time such as 2 to 4 weeks by a second immunization (boost) using a second strain with a different fH antigen or no fH antigen. The live vaccine compositions are suitable for oral administration to an individual to provide protection from Avian *Influenza*.

Preferably, a vaccine composition comprises a suspension of a live bacterial strain described herein in a physiologically accepted buffer or saline solution that can be swallowed from the mouth of an individual. However, oral administration of a vaccine composition to an individual may also include, without limitation, administering a suspension of a bacterial vaccine strain described herein through a nasojejunal or gastrostomy tube and administration of a suppository that releases a live bacterial vaccine strain to the lower intestinal tract of an individual.

4. Definitions

In order that the invention may be more fully understood, the following terms are defined.

As used herein, "attenuated", "attenuation", and similar terms refer to elimination or reduction of the natural virulence of a bacterium in a particular host organism, such as a mammal. "Virulence" is the degree or ability of a pathogenic microorganism to produce disease in a host organism. A bacterium may be virulent for one species of host organism (e.g., a mouse) and not virulent for another species of host organism (e.g., a human). Hence, broadly, an "attenuated" bacterium or strain of bacteria is attenuated in virulence toward at least one species of host organism that is susceptible to infection and disease by a virulent form of the bacterium or strain of the bacterium. As used herein, the term "genetic locus" is a broad term and comprises any designated site in the genome (the total genetic content of an organism) or in a particular nucleotide sequence of a chromosome or replicating nucleic acid molecule (e.g., a plasmid), including but not limited to a gene, nucleotide coding sequence (for a protein or RNA), operon, regulon, promoter, regulatory site (including transcriptional terminator sites, ribosome binding sites, transcriptional inhibitor binding sites, transcriptional activator binding sites), origin of replication, intercistronic region, and portions therein. A genetic locus may be identified and characterized by any of a variety of in vivo and/or in vitro methods available in the art, including but not limited to, conjugation studies, crossover frequencies, transformation analysis, transfection analysis, restriction enzyme mapping protocols, nucleic acid hybridization analyses, polymerase chain reaction (PCR) protocols, nuclease protection assays, and direct nucleic acid sequence analysis. As used herein, the term "infection" has the meaning generally used and understood by persons skilled in the art and includes the invasion and multiplication of a microorganism in or on a host organism ("host", "individual", "patient") with or without a manifestation of a disease (see, "virulence" above). Infectious microorganisms include pathogenic viruses, such as Avian *Influenza,* that can cause serious diseases when infecting an unprotected individual. An infection may occur at one or more sites in or on an individual. An infection may be unintentional (e.g., unintended ingestion, inhalation, contamination of wounds, etc.) or intentional (e.g., administration of a live vaccine strain, experimental challenge with a pathogenic vaccine strain). In a vertebrate host organism, such as a mammal, a site of infection includes, but is not limited to, the respiratory system, the alimentary canal (gut), the circulatory system, the skin, the endocrine system, the neural system, and intercellular spaces. Some degree and form of replication or multiplication of an infective microorganism is required for the microorganism to persist at a site of infection. However, replication may vary widely among infecting microorganisms. Accordingly, replication of infecting microorganisms comprises, but is not limited to, persistent and continuous multiplication of the microorganisms and transient or temporary maintenance of microorganisms at a specific location. Whereas "infection" of a host organism by a pathogenic microorganism is undesirable owing to the potential for causing disease in the host, an "infection" of a host individual with a live vaccine comprising genetically altered, attenuated *Salmonella* bacterial strain as described herein is desirable because of the ability of the bacterial strain to elicit a protective immune response to antigens of Avian *Influenza* virus that cause avian *influenza* in humans and other mammals.

As used herein, the terms "disease" and "disorder" have the meaning generally known and understood in the art and comprise any abnormal condition in the function or well being of a host individual. A diagnosis of a particular disease or disorder, such as Avian *Influenza,* by a healthcare professional may be made by direct examination and/or consideration of results of one or more diagnostic tests.

A "live vaccine composition", "live vaccine", "live bacterial vaccine", and similar terms refer to a composition comprising a strain of live *Salmonella* bacteria that expresses at least one antigen of Avian *Influenza,* e.g., the H antigen, the N antigen, or a combination thereof, such that when administered to an individual, the bacteria will elicit an immune response in the individual against the Avian *Influenza* antigen(s) expressed in the *Salmonella* bacteria and, thereby, provide at least partial protective immunity against Avian *Influenza.* Such protective immunity may be evidenced by any of a variety of observable or detectable conditions, including but not limited to, diminution of one or more disease symptoms (e.g., respiratory distress, fever, pain, diarrhea, bleeding, inflammation of lymph nodes, weakness, malaise), shorter duration of illness, diminution of tissue damage, regeneration of healthy tissue, clearance of pathogenic microorganisms from the individual, and increased sense of well being by the individual. Although highly desired, it is understood by persons skilled in the art that no vaccine is expected to induce complete protection from a disease in every individual that is administered the vaccine or that protective immunity is expected to last throughout the lifetime of an individual without periodic "booster" administrations of a vaccine composition. It is also understood that a live vaccine comprising a bacterium described herein may be, at the discretion of a healthcare professional, administered to an individual who has not presented symptoms of Avian Influenza but is considered to be at risk of infection or is known to already have been exposed to Avian influenza virus, e.g., by proximity or contact with Avian Influenza patients or virally contaminated air, liquids, or surfaces.

The terms "oral", "enteral", "enterally", "orally", "non-parenteral", "non-parenterally", and the like, refer to administration of a compound or composition to an individual by a route or mode along the alimentary canal. Examples of "oral" routes of administration of a vaccine composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g., using suppositories that release a live bacterial vaccine strain described herein to the lower intestinal tract of the alimentary canal.

The term "recombinant" is used to describe non-naturally altered or manipulated nucleic acids, cells transformed, electroporated, or transfected with exogenous nucleic acids, and polypeptides expressed non-naturally, e.g., through manipulation of isolated nucleic acids and transformation of cells. The term "recombinant" specifically encompasses nucleic acid molecules that have been constructed, at least in part, in vitro using genetic engineering techniques, and use of the term "recombinant" as an adjective to describe a molecule, construct, vector, cell, polypeptide, or polynucleotide specifically excludes naturally existing forms of such molecules, constructs, vectors, cells, polypeptides, or polynucleotides.

Cassette, or expression cassette is used to describe a nucleic acid sequence comprising (i) a nucleotide sequence encoding a promoter, (ii) a first unique restriction enzyme cleavage site located 5' of the nucleotide sequence encoding the promoter, and (iii) a second unique restriction enzyme cleavage site located 3' of the nucleotide sequence encoding the promoter. The cassette may also contain a multiple cloning site (MCS) and transcriptional terminator within the 5' and 3' restriction endonuclease cleavage sites. The cassette may also contain cloned genes of interest.

As used herein, the term "*salmonella*" (plural, "salmonellae") and "*Salmonella*" refers to a bacterium that is a serovar of *Salmonella enterica*. A number of serovars of *S. enterica* are known. Particularly preferred *Salmonella* bacteria useful in the invention are attenuated strains of *Salmonella enterica* serovar *Typhimurium* (*S. typhimurium*) and serovar *Typhi* (*S. typhi*) as described herein. As used herein, the terms "strain" and "isolate" are synonymous and refer to a particular isolated bacterium and its genetically identical progeny. Actual examples of particular strains of bacteria developed or isolated by human effort are indicated herein by specific letter and numerical designations (e.g. strains Ty21a, CMV906, CMV908, CMV906-htr, CMV908-htr, Ty800, holavax, M01ZH09, VNP20009).

The definitions of other terms used herein are those understood and used by persons skilled in the art and/or will be evident to persons skilled in the art from usage in the text. This invention provides live vaccine compositions for protecting against Avian *Influenza* comprising live *Salmonella enterica* serovars that are genetically engineered to express one or more Avian *Influenza* antigen polypeptides, such as the H1, H5, H5 (H274Y), H7 or H9 and N1, N2 and N7 antigens of Avian *Influenza* virus.

BRIEF DESCRIPTION OF THE DRAWINGS

FIG. 5 shows a plasmid vector for expression of an antigen (e.g., H5 or N1) as a ClyA fusion.

FIG. 6 shows a plasmid vector for expression of an antigen (e.g., H5 or N1) as a autotransporter fusion.

DETAILED DESCRIPTION OF THE INVENTION

Figure 1:
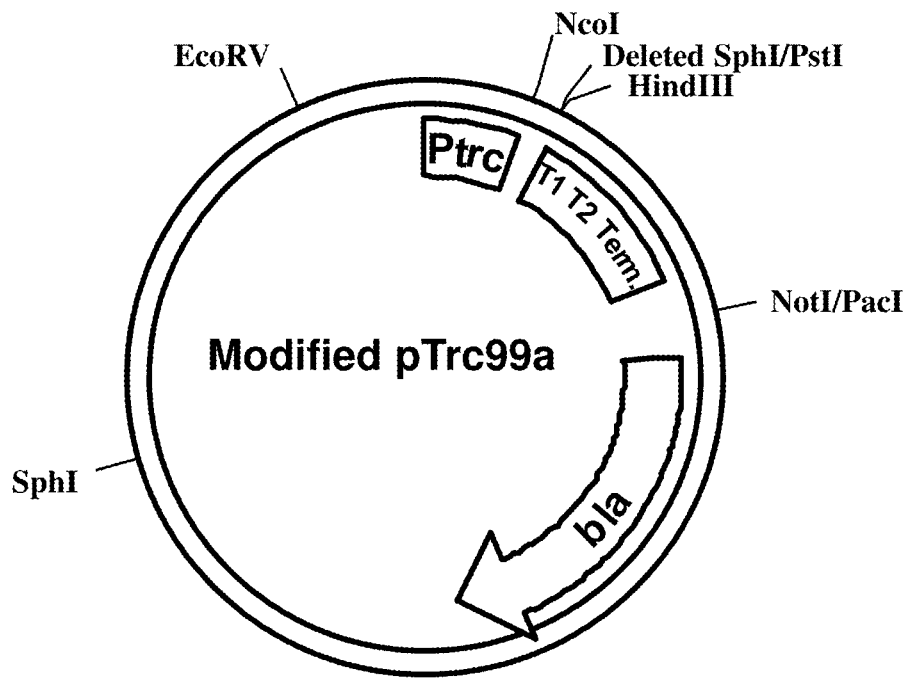
FIG. 1 shows a modified ptrc99a plasmid.

The present invention is based upon a combination of bacterial vector and protein expression technology which results in a unique vaccine which is rapidly constructed in response to emerging avian *influenza* and their highly pathogenic derivatives. The present invention is directed to the construction bacterially codon optimized avian and human *Influenza* genes and their incorporation into a *Salmonella* strain for therapeutic use in the prevention of avian *influenza* and highly pathogenic derivatives. An antigen-expressing plasmid or chromosomal construct in the bacterial strains described herein may also contain one or more transcriptional terminators adjacent to the 3' end of a particular nucleotide sequence on the plasmid to prevent undesired transcription into another region of the plasmid or chromosome. Such transcription terminators thus serve to prevent transcription from extending into and potentially interfering with other critical plasmid functions, e.g., replication or gene expression. Examples of transcriptional terminators that may be used in the antigen-expressing plasmids described herein include, but are not limited to, the TI and T2 transcription terminators from 5S ribosomal RNA bacterial genes (see, e.g., FIGS. 1-5; Brosius and Holy, Proc.

Natl. Acad. Sci. USA, 81: 6929-6933 (1984); Brosius, Gene, 27(2): 161-172 (1984); Orosz et al., Eur. J Biochem., 20 (3): 653-659 (1991)).

The mutations in an attenuated bacterial host strain may be generated by integrating a homologous recombination construct into the chromosome or the endogenous *Salmonella* virulence plasmid (Donnenberg and Kaper, 1991; Low et al. (Methods in Molecular Medicine, 2003)). In this system, a suicide plasmid is selected for integration into the chromosome by a first homologous recombination event, followed by a second homologous recombination event which results in stable integration into the chromosome. The antigen-expressing chromosomal integration constructs described herein comprise one or more nucleotide sequences that encode one or more polypeptides that, in turn, comprise one or more Avian *Influenza* antigens, such as the hemagglutinin and neuraminidase polypeptide antigens, or immunogenic portions thereof, from Avian *Influenza* virus and highly pathogenic derivatives. Such coding sequences are operably linked to a promoter of transcription that functions in a *Salmonella* bacterial strain even when such a bacterial strain is ingested, i.e., when a live vaccine composition described herein is administered orally to an individual. A variety of naturally occurring, recombinant, and semi-synthetic promoters are known to function in enteric bacteria, such as *Escherichia coli* and serovars of *S. enterica* (see, e.g., Dunstan et al., Infect. Immun., 67(10): 5133-5141 (1999)). Promoters (P) that are useful in the invention include, but are not limited to, well known and widely used promoters for gene expression such as the naturally occurring Plac of the lac operon and the semi-synthetic Ptrc (see, e.g., Amman et al., Gene, 25 (2-3): 167-178 (1983)) and Ptac (see, e.g., Aniann et al., Gene, 69(2): 301-315 (1988)), as well as PpagC (see, e.g., Hohmann et al., Proc. Natl. Acad. Sci. USA, 92. 2904-2908 (1995)), PpmrH (see, e.g., Gunn et al., Infect. Immun., 68: 6139-6146 (2000)), PpmrD (see, e.g., Roland et al., J Bacteriol., 176: 3589-3597 (1994)), PompC (see, e.g., Bullifent et al., Vaccine, 18: 2668-2676 (2000)), PnirB (see, e.g., Chatfield et al., Biotech. (NY), 10: 888-892 (1992)), PssrA (see, e.g., Lee et al., J Bacteriol. 182. 771-781 (2000)), PproU (see, e.g., Rajkumari and Gowrishankar, J Bacteriol., 183. 6543-6550 (2001)), Pdps (see, e.g., Marshall et al., Vaccine, 18: 1298-1306 (2000)), and PssaG (see, e.g., McKelvie et al., Vaccine, 22: 3243-3255 (2004)), Some promoters are known to be regulated promoters that require the presence of some kind of activator or inducer molecule in order to transcribe a coding sequence to which they are operably linked. However, some promoters may be regulated or inducible promoters in *E. coli*, but function as unregulated promoters in *Salmonella*. An example of such a promoter is the well known trc promoter ("Ptrc", see, e.g., Amman et al., Gene, 25(2-3): 167-178 (1983); Pharmacia-Upjohn). As with Plac and Ptac, Ptrc functions as an inducible promoter in *Escherichia coli* (e.g., using the inducer molecule isopropyl-p-D-1 8 thio-galactopyranoside, "IPTG"), however, in *Salmonella* bacteria having no Lad repressor, Ptrc is an efficient constitutive promoter that readily transcribes Avian *Influenza* antigen-containing polypeptide coding sequences present on antigen-expressing plasmids described herein. Accordingly, such a constitutive promoter does not depend on the presence of an activator or inducer molecule to express an antigen-containing polypeptide in a strain of *Salmonella*.

The Avian *Influenza* antigen-expressing chromosomal integration constructs which integrate into the live vaccine strains also contain an origin of replication (ori) that enables the precursor plasmids to be maintained as multiple copies in certain the bacterial cells which carry the lambda pir element. For the process of cloning DNA, a number of multi-copy plasmids that replicate in *Salmonella* bacteria are known in the art, as are various origins of replications for maintaining multiple copies of plasmids. Preferred origins of replications for use in the multi-copy antigen-expressing plasmids described herein include the origin of replication from the multi-copy plasmid pBR322 ("pBR ori"; see, e.g., Maniatis et al., In Molecular Cloning: A Laboratory Manual (Cold Spring Harbor Laboratory, Cold Spring Harbor, 1982), pp. 479-487; Watson, Gene, 70: 399-403, 1988), the low copy origin of replication from pACYC177, and the origin of replication of pUC plasmids ("pUC ori"), such as found on plasmid pUC 1 8 (see, e.g., Yanish-Perron et al., Gene, 33: 103-119 (1985)). Owing to the high degree of genetic identity and homology, any serovar of *S. enterica* may be used as the bacterial host for a live vaccine composition for Avian *Influenza*, provided the necessary attenuating mutations and antigen-expressing plasmids as described herein are also employed. Accordingly, serovars of *S. enterica* that may be used in the invention include those selected from the group consisting of *Salmonella enterica* serovar *Typhimurium* (*S. typhimurium*), *Salmonella montevideo*, *Salmonella enterica* serovar *Typhi* (*S. typhi*), *Salmonella enterica* serovar *Paratyphi B* (*S. paratyphi B*), *Salmonella enterica* serovar *Paratyphi C* (*S. paratyphi C*), *Salmonella enterica* serovar *Hadar* (*S. Hadar*), *Salmonella enterica* serovar *Enteriditis* (*S. enteriditis*), *Salmonella enterica* serovar *Kentucky* (*S. kentucky*), *Salmonella enterica* serovar *Infantis* (*S. infantis*), *Salmonella enterica* serovar *Pullorum* (*S. pullorum*), *Salmonella enterica* serovar *Gallinarum* (*S. gallinarum*), *Salmonella enterica* serovar *Muenchen* (*S. muenchen*), *Salmonella enterica* serovar *Anaturn* (*S. anatum*), *Salmonella enterica* serovar *Dublin* (*S. dublin*), *Salmonella enterica* serovar *Derby* (*S. derby*), *Salmonella enterica* serovar *Choleraesuis* var. *kunzendorf* (*S. cholerae kunzendorf*), and *Salmonella enterica* serovar *minnesota* (*S. Minnesota*).

The vaccine compositions described herein may be administered orally to an individual in any form that permits the *Salmonella* bacterial strain of the composition to remain alive and to persist in the gut for a time sufficient to elicit an immune response to one or more Avian *Influenza* antigens of Avian *Influenza* virus and highly pathogenic derivatives expressed in the *Salmonella* strain. For example, the live bacterial strains described herein may be administered in relatively simple buffer or saline solutions at physiologically acceptable pH and ion content. By "physiologically acceptable" is meant whatever is compatible with the normal functioning physiology of an individual who is to receive a live vaccine composition described herein.

Preferably, bacterial strains described herein are suspended in otherwise sterile solutions of bicarbonate buffers, phosphate buffered saline (PBS), or physiological saline, that can be easily swallowed by most individuals. However, "oral" routes of administration may include not only swallowing from the mouth a liquid suspension or solid form comprising a live bacterial strain described herein, but also administration of a suspension of a bacterial strain through a nasojejunal or gastrostomy tube, and rectal administration, e.g., by using a suppository comprising a live bacterial strain described herein to establish an infection by such bacterial strain in the lower intestinal tract of the alimentary canal. Accordingly, any of a variety of alternative modes and means may be employed to administer a vaccine composition described herein to the alimentary canal of an individual if the individual cannot swallow from the mouth.

In a preferred embodiment of the invention, the bacteria have genetic modifications which result in the expression of at least one hemagglutinin and one neuraminidase, where each gene is optimized for bacterial expression in at least one codon. In a most preferred embodiment, the hemagglutinin and neuraminidase genes are further modified to be secreted by the bacteria as heterologous fusion proteins. In a most preferred embodiment, the neuraminidase and hemagglutinin heterologous fusion proteins are integrated into the chromosome in delta IS200 sites.

In a preferred embodiment, the bacterial strains are genetically stabilized by deletion of IS200 elements, which reduces their genetic recombination potential.

In another embodiment, the bacterial strains are genetically stabilized by deletion of phage and prophage elements, which reduces their genetic recombination and transduction potential.

In another embodiment, the bacterial strains are genetically isolated from phage infection by constitutive expression of the P22 C2 repressor, which reduces their ability to be infected by phage and the subsequent transduction of genes by such phage.

In another embodiment, the bacterial strains have genetically defined flagellar antigens, or no flagellar antigens, which reduces the immune system elimination of the vector, enhancing its immunization potential in second immunizations.

In a preferred embodiment, the genetically modified bacteria are used in animals, including humans, birds, dogs and pigs, for protection against avian *influenza* and highly pathogenic derivatives.

In another embodiment, a kit allows for rapid construction of a bacterial vaccine which is closely matched to an emerging Avian *Influenza* or its highly pathogenic derivative.

FIG. 1 shows a modified ptrc99a plasmid. The SphI site within the multiple cloning site has been deleted making the upstream SphI site unique and useful for subcloning into pCVD vectors. In addition, NotI and PacI sites are added downstream of the $t_1t_2$ terminators also for use in subcloning into pCVD vectors.

Figure 2A:
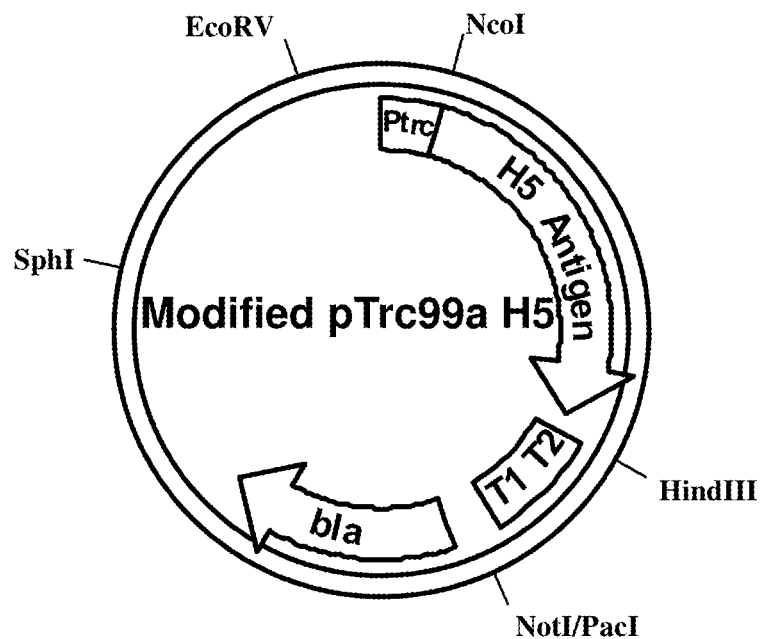
FIGS. 2A and 2B show a plasmid vectors capable of expressing the H5 or N1 antigens cytoplasmically.
Figure 2B:
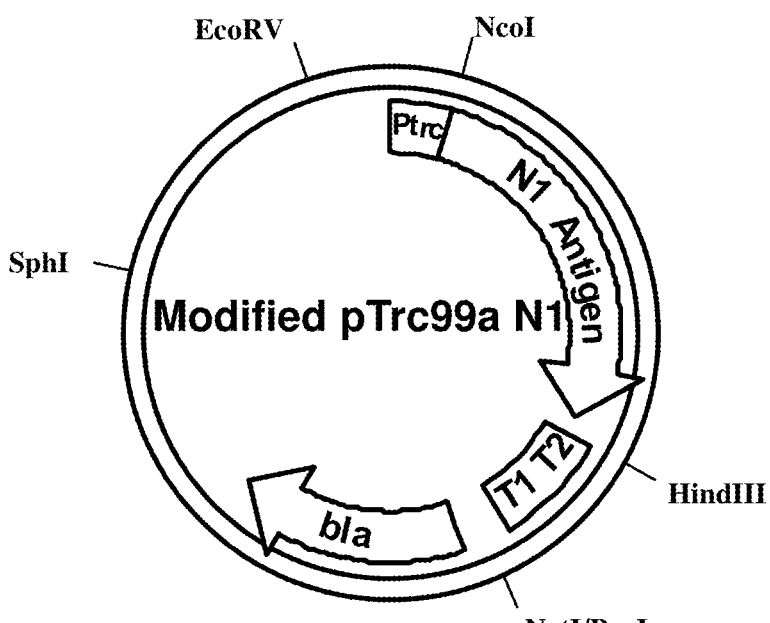

FIG. 2A and B show a plasmid vectors capable of expressing the H5 or N1 antigens cytoplasmically. "Ptrc" refers to a functional trc promoter operably linked to a structural coding sequence for an H5 antigen fusion polypeptide. "TI T2" refers to the TI and T2 transcriptional terminators of the 5S bacterial ribosomal RNA gene. "bla" refers to the beta-lactamase gene for ampicillin and carbenicillin resistance. Arrows indicate direction of transcription. See text for details.

Figure 3:
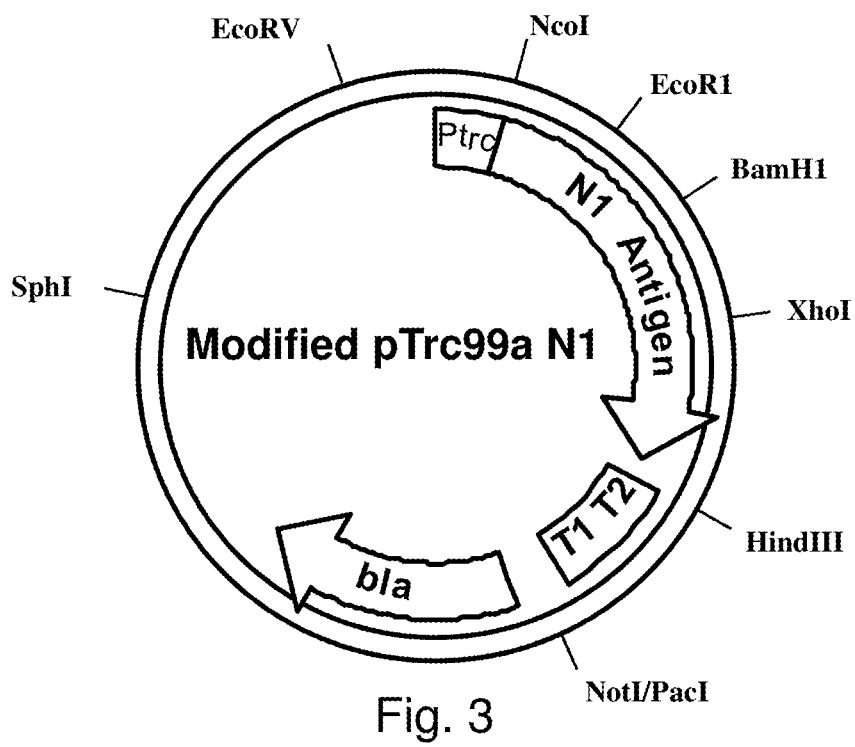
FIG. 3 shows modified ptrc99a plasmid with unique restriction sites engineered into the coding sequence of the N1 gene for rapid exchange of mutations such as the H274Y.

FIG. 3 shows modified ptrc99a plasmid with unique restriction sites engineered into the coding sequence of the N1 gene for rapid exchange of mutations such as the H274Y.

Figure 4A:
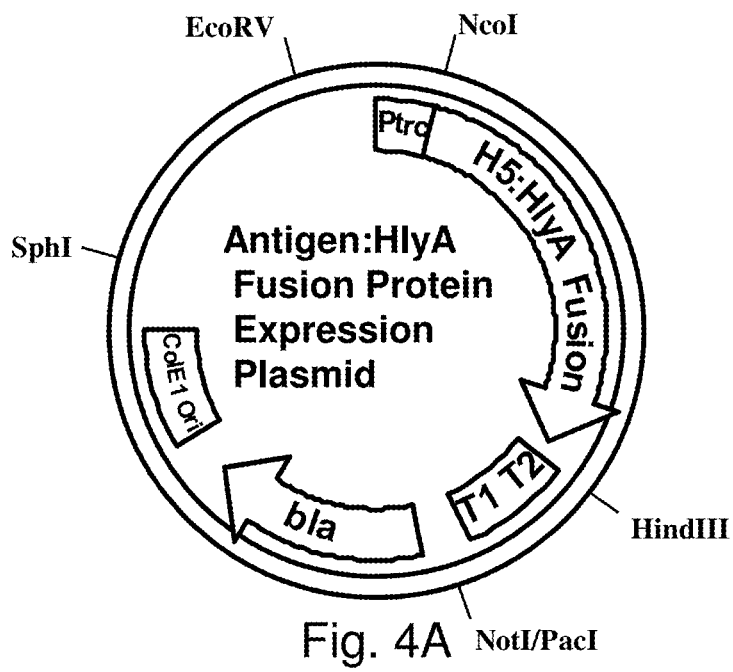
FIG. 4A shows a plasmid vectors expressing the H5 or N1 antigens in a secreted form as fusions with the hlyA protein.
Figure 4B:
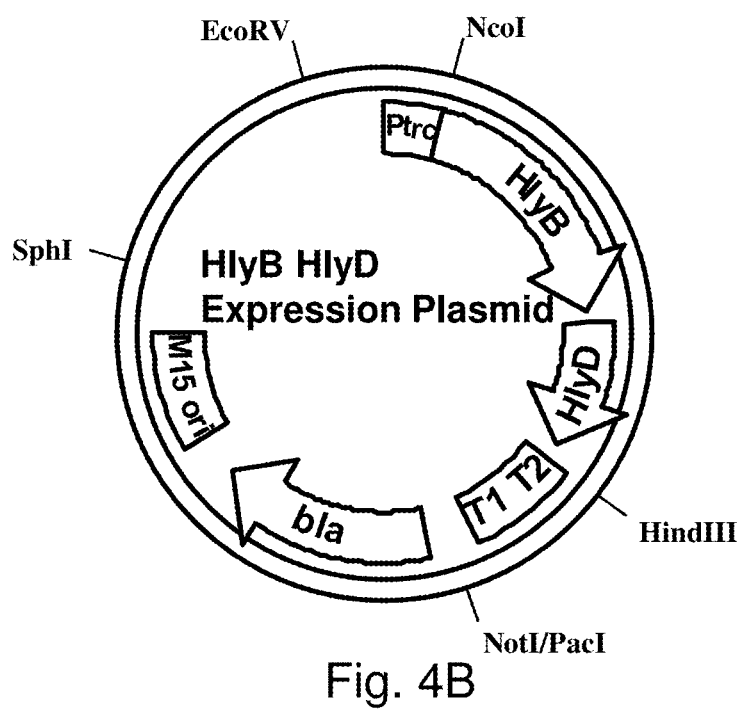
FIG. 4B shows a plasmid vector expressing HlyB and HlyD genes necessary for secretion of HlyA and HlyA fusion proteins.

FIG. 4A shows a plasmid vectors expressing an antigen (H5 or N1) in a secreted form as fusions with the hlyA protein. Numbers after names of restriction endonucleases indicate specific restriction sites in the plasmid. "Ptrc" refers to a functional trc promoter operably linked to a structural coding sequence for an antigen fusion polypeptide. "ColE1 ori" refers to the colicin E1 origin of replication. 4B shows the hemolysin secretion HlyB and HlyD proteins in a plasmid vector with a different origin of replication, the "M15ori", which refers the M15 origin of replication. See text for details.

FIG. 5 shows ClyA fusion. A plasmid vector for expression of an antigen (e.g., H5 or N1) as a ClyA fusion is shown. The modified trc99a vector of FIG. 1 is used as a cloning and expression vector for a ClyA:antigen fusion.

FIG. 6 shows Autotransporter fusion. A plasmid vector for expression of an antigen (e.g., H5 or N1) as an autotransporter (translocator) fusion is shown. The modified trc99a vector of FIG. 1 is used as a cloning and expression vector for the autotransporter:antigen fusion. "S" refers to a hydrophobic signal sequence.

Figure 7:
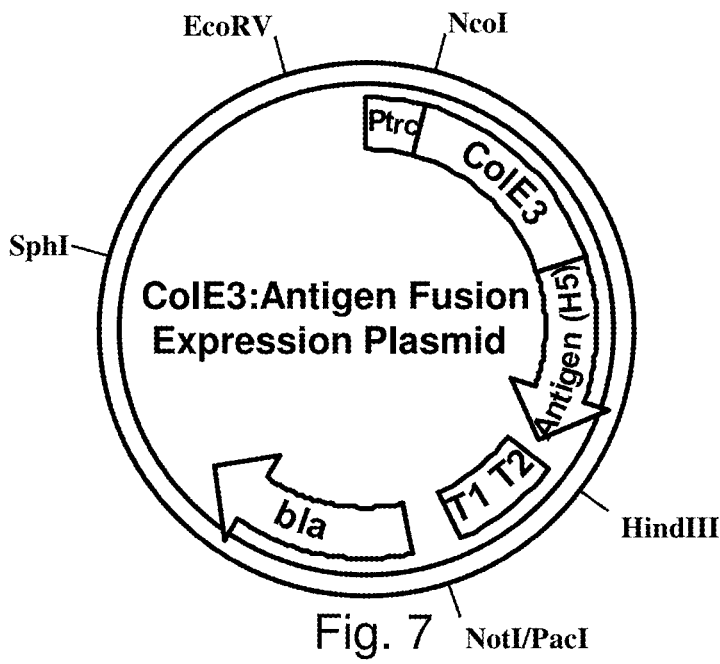
FIG. 7 shows a plasmid vector for expression of an antigen (e.g., H5 or N1) as a colicin E3 fusion.

FIG. 7 shows Colicin E3 (ColE3) fusion. A plasmid vector for expression of an antigen (e.g., H5 or N1) as a colicin E3 fusion is shown. The modified trc99a vector of FIG. 1 is used as a cloning and expression vector for the ColE3:antigen fusion.

Figure 8A:
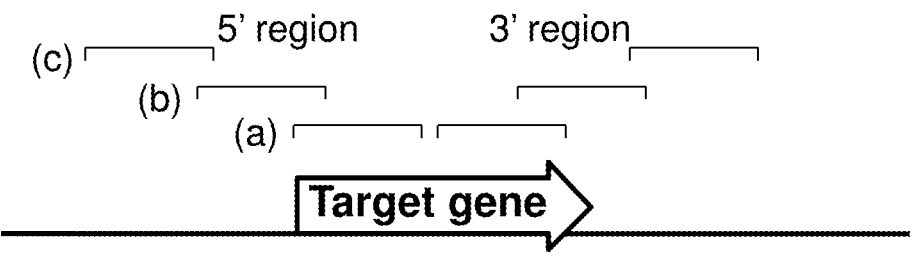
FIG. 8A shows selection of 5' and 3' DNA segments for constructing a pCVD442 chromosomal integration vector.
Figure 8B:
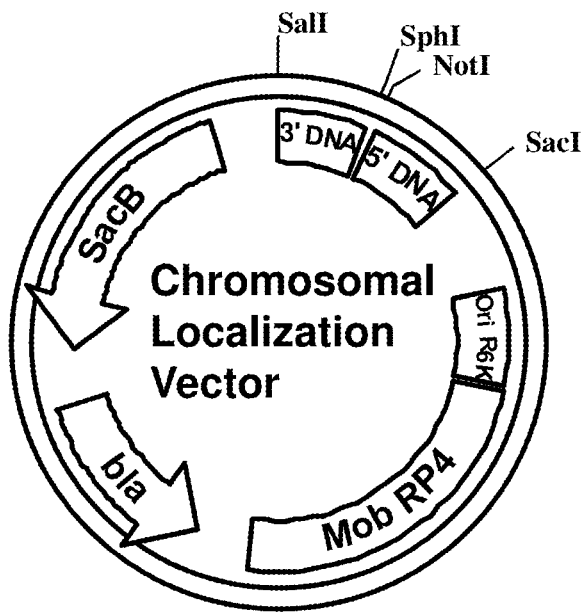
FIG. 8B shows the vector for disrupting chromosomal genes and capable of integration of new genes into the chromosome.

FIGS. 8A and 8B show pCVD knockout constructs. FIG. 8A shows selection of 5' and 3' DNA segments for constructing a pCVD442 chromosomal integration vector for disrupting chromosomal genes and integration of new genes into the chromosome. The 5' and 3' segments may be selected completely within the gene (a), partly within and partly outside (b) or completely outside (c) or any combination of the above so long as in each case there is a gap of at least one nucleotide such that the recombination event results in such gap introduced into the gene as a deletion resulting in inactivation of the gene. When a foreign gene is inserted such as in FIG. 8B, then the inserted gene also results in a gene disruption following integration and resolution. FIG. 8B shows a localization vector with 5' and 3' sequence flanking a multiple-cloning sites (SphI/NotI) into which an expression cassette containing a gene of interest (e.g., an antigen such as H5 or N1, or another gene of interest such as the P22 phage C2 phage repressor protein).

Figure 9A:
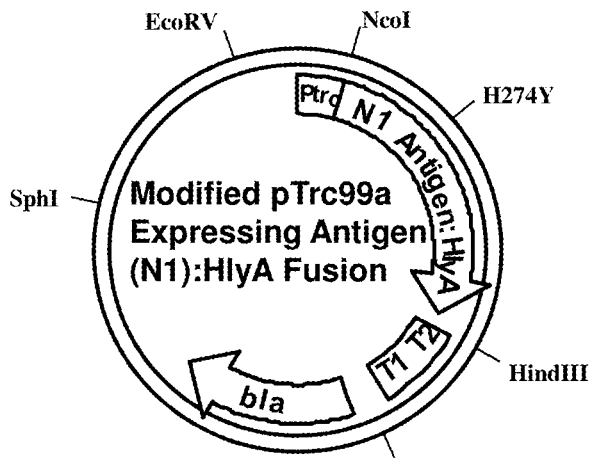
FIGS. 9A and 9B show a cloning sequence, from a synthetic gene expression vector (FIG. 9A) to a chromosomal localization vector (FIG. 9B).
Figure 9B:
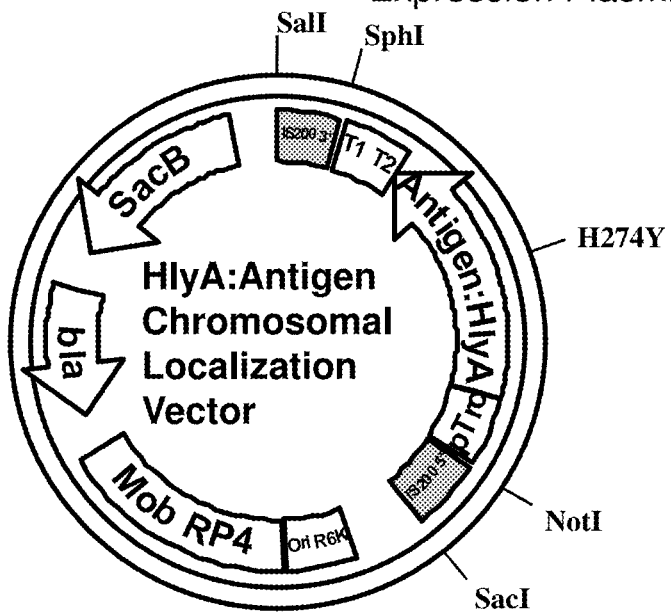

FIGS. 9A and 9B show a cloning sequence, from FIG. 9A, synthetic gene within the expression vector to FIG. 9B, chromosomal localization vector. First, a synthetic gene is generated using standard molecular techniques, the gene is then cloned into an expression vector and then subcloned into a pCVD vector for chromosomal localization. "H274Y" refers to the histidine to tyrosine mutation that confers oseltamivir resistance.

Figures 10A, 10B:
FIGS. 10A and 10B show PCR method for determination of IS200 17.7 and 19.9 rearrangement/deletion using forward and reverse primers P1 and P2.

FIGS. 10A and 10B show a determination of IS200 17.7 and 19.9 rearrangement/deletion. The Suwwan deletion is a recombination event between two IS200 elements located at 17.7 and 19.9 Cs. If oligonucleotide primers are generated (P1; forward) to unique sequences before the 17.7 and (P2; reverse) after the 19.9, no PCR product will be generated under standard short PCR conditions (typically 500 bp to 10,000 bp) because the distance between the two points is too long (greater than 20,000 bp). However, following a Suwwan deletion, the two points are in relative close proximity and a PCR product will readily be generated.

Figure 11A:
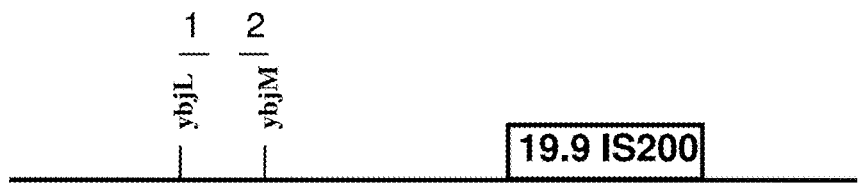
FIGS. 11A, 11B, 11C and 11D show a representation of a method to achieve the Suwwan deletion in strains lacking the 17.7 Cs IS200.
Figure 11B:
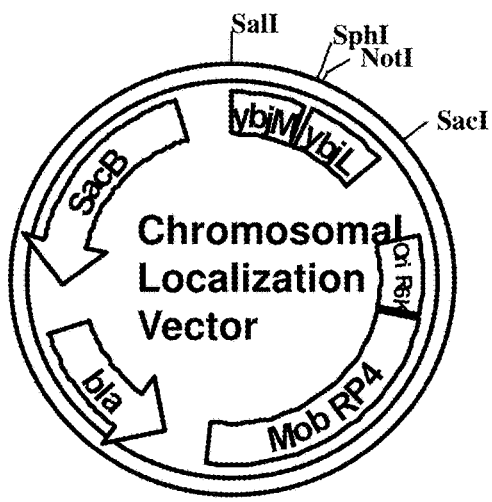
Figure 11C:
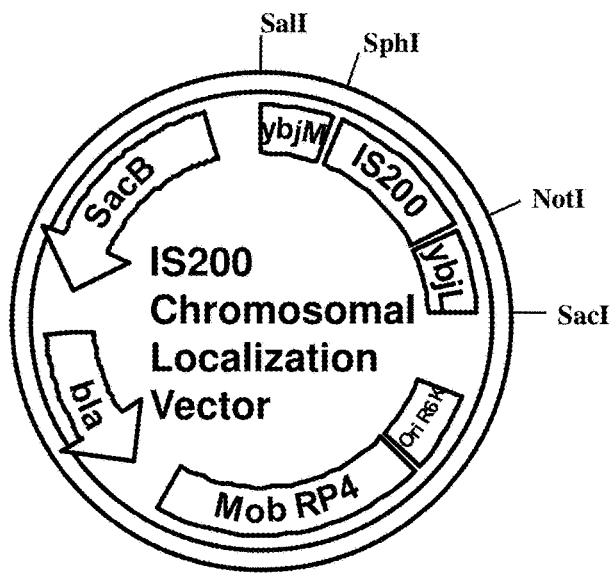
Figure 11D:

FIGS. 11A, 11B, 11C and 11D show a method to generate strains capable of undergoing the Suwwan deletion in strains lacking the 17.7 Cs IS200. In strains which lack the 17.7 Cs IS200, an IS200 can be introduced in order to generate the potential to undergo such a deletion. As depicted in FIGS. 8A and 8B, a chromosomal localization vector derived from pCVD442 can be generated with cloning sites (SphI/NotI) which will accommodate foreign DNA. In order to insert an IS200 in the DNA sequence in the homologous location to that of *Salmonella typhimurium* ATCC 14028 is identified as shown in FIG. 11A between the genes ybjL (1) and ybjM (2) and the DNA flanking that region is cloned as 5' and 3' regions into pCVD442 together with the SphI and NotI cloning sites as shown in FIG. 11B and the IS200 from ATCC 14028 is cloned in between the 5' and 3' regions as shown in FIG. 11C. Recombination with the chromosome results in the insertion of the IS200 at the appropriate location as shown in FIG. 11D allowing for the potential to spontaneously recombine as shown in FIGS. 10A and 10B.

1.1 Cloning Avian Influenza Antigens for Bacterial Expression.

As described in the present invention, Avian *Influenza* genes can be cloned as a codon-optimized synthetic DNA construct and expressed in bacteria including but not limited to *Salmonella*. Cloning and expression of the avian *influenza* genes uses standard molecular techniques (Sambrook et al., Molecular Cloning, Cold Spring Harbor Laboratory Press, 1989) and conventional bacterial expression plasmids such as pTrc99a (Pharmacia-Upjohn). This results in a plasmid-based, cytosolic expression of the antigen. For an example, see Section 2.1. The Avian *Influenza* antigens can be further modified for secretion as heterologous fusions. Such fusions can be with previously described for hlyA, clyA, SPATE autotransporter proteins or a novel composition of a fusion with colicin E3 (colE3). For example, see Section 2.10. These cytosolic and secreted constructs can be further modified by integration into the bacterial chromosome using standard techniques of targeted homologous recombination (Donnenberg and Kaper, 1991) where the bacterial expression cassette is inserted in between the 5' and 3' flanking sequences as further described below.

1.2 Improvement of Genetic Stability

Bacterial strains such as *Salmonella* contain a variety of phage and prophage elements. Activation of such phage elements can result in genetic rearrangements and/or liberate such phage as Gifsy and Fels which are capable of transducing other bacterial strains. Such phage elements are known by DNA sequence of entire genomes. If the genome sequence is unknown, such elements may be determined by low stringency DNA:DNA hybridization. In the present invention, DNA sequences associated with phage and prophage elements are disrupted to improve genetic stability and reduce the potential for transduction. Genetic stability is improved by deletion of IS200 and phage/prophage elements. Deletion of IS200 and phage/prophage elements on the bacterial chromosome is accomplished using standard techniques of targeted homologous recombination (Donnenberg and Kaper, 1991) where 5' and 3' flanking sequences of the deletion target (IS200 or phage/prophage elements) are cloned into the pCVD442 vector.

Improvement of genetic stability can be determined by assay of phenotypic or genotypic properties such as spontaneous rearrangement of IS200 elements resulting in chlorate resistance (Murray et al., 2004). The ability to rearrange IS200 elements and cause a spontaneous deletion may be determined by assay of spontaneous chlorate resistant bacterial colonies on LB media containing chlorate. These colonies are then subjected to PCR analysis of the genome, combined with DNA sequencing, which is thus definitive in respect to a particular IS200-based deletion in the 17.7 to 19.9 Cs region (See FIG. 8). This and other DNA rearrangements, duplications and deletions are also determined by pulse-field gel electrophoresis which compares the DNA banding pattern of the parent strain (control strain) to strains in which rearrangements are to be determined (test strains).

1.3 Genetic Isolation of the Bacterial Vectors from Phage

The bacterial strains which vector the avian *influenza* antigens can be altered to genetically isolate them from phage. Genetic isolation is accomplished by limiting the phage integration through constitutive expression of the P22 phage repressor. When exogenous phage enter the repressor inhibits their integration into the chromosome. Under certain circumstances, the repressor may be proteolyticly cleaved by the RecA protein. This may be circumvented by eliminating the RecA protein cleavage site through site-directed mutagenesis (Sambrook et al., Molecular Cloning, Cold Spring Harbor Laboratory Press, 1989). The P22 repressor is cloned into a bacterial expression vector, such as the trc99a vector and results in constitutive expression. The expression cassette may be further modified to be integrated into the chromosome using standard techniques of targeted homologous recombination (Donnenberg and Kaper, 1991) where the trc99a expression cassette is cloned between the 5' and 3' flanking sequences of a deletion target (e.g., IS200 or phage/prophage elements) within a pCVD442 vector. Genetic isolation is tested by experimental infection with phage to which the bacteria are normally susceptible. Successful construction of a genetically isolated strain is recognized by substantially lower infection rates (e.g., 10 fold lower or more) compared to the parent strain, where infection rates are determined by plaque forming units (PFU) of phage, such as P22 phage. Moreover, the transduction potential of such bacteria is also assayed using standard techniques know to those skilled in the arts, such as the comparison of transducing potential for a metabolic gene (e.g., purI) from the parent strain compared to the modified strain to an identical recipient strain deficient in the same metabolic gene (e.g., delta purI). The genetically isolated strains show substantially lower (e.g., 10 fold lower or more) ability to have a representative gene transduced to another strain compared to the parent strain.

1.4 Construction of Bacteria with Genetically Defined Flagellar (fH) Antigens or No fH Antigens.

In another embodiment, the bacterial strains have genetically defined flagellar antigens, or no flagellar antigens, which reduces the immune system elimination of the vector, enhancing its immunization potential in second immunizations. Strains with defined flagellar antigens are constructed by first selecting substrains that express either the fH1 or fH2 antigens which the bacteria spontaneously generate by inversion of a portion of the gene mediated by the Hin recombinase. To select strains expressing either fH1 or fH2, the bacteria are plated to standard growth media and subjected to a colony lift using nitrocellulose or equivalent membrane binding matrix, followed by lysis and blocking of the membrane. fH1 and fH2 are selected using fH1 and fH2 antibodies. The corresponding clone is then purified. These clones are further subjected to deletion of the Hin recombinase gene using standard homologous recombination techniques including lambda red recombinase or pCVD vectors specific for disrupting Hin, thus fixing their flagellar antigen expression. Furthermore, strains without any flagellar antigens may be constructed by deletion of the fliBC genes using standard homologous recombination. These genetically altered strains with stable expression of either fH1, fH2 or no flagellar antigens (fH0) have reduced elimination by the immune system when they are used for second immunizations where the first immunization is a bacterial strain with a different flagellar antigen or no flagellar antigen or where the first immunization is a non-bacterial vaccine including an egg-based vaccine.

1.5 Use of Genetically Modified Bacteria for Protection Against Avian Influenza and Highly Pathogenic Derivitives.

As described in the present invention, the bacterial strains which vector the H and N antigens of Avian *Influenza* and highly pathogenic derivatives are useful as vaccines, resulting protection against infection by *Influenza* strains.

1.6 A Kit for Rapidly Producing Genetically Modified Bacteria for Protection Against Avian Influenza and Highly Pathogenic Derivatives.

A kit according to one embodiment of the invention comprises 1) a bacterial strain, 2) pTrc99a expression vectors containing A) neuraminidase and B) hemagglutinin antigens with unique restriction endonuclease enzymes within the sequence which allows rapid exchange of small segments (such as the N1 amino acid 274) and 3) multiple unique chromosomal localization vectors targeting a variety of genes including IS200s, phage elements (especially Gifsy and Fels) and metabolic genes (such as purI, AroA, etc) for insertion of the pTrc99a expression cassettes with the modified H and N antigens.

In order to more fully illustrate the invention, the following non-limiting examples are provided.

Examples of Bacterial Expression of H And N Antigens and Incoporation in Genetically Stabilized and Isolated Strains with Defined Flagellar Antigens and Their use in Protection Against Avain Influenza and Highly Pathogenic Derivitives.

2.1 Example of Methods for Obtaining Bacterial Strains of the Appropriate Genetic Background.

Bacterial strains useful in the invention include strains of known safety when administered to humans including but not limited to Ty21a, CMV906, CMV908, CMV906-htr, CMV908-htr, Ty800, holavax, M01ZH09, VNP20009. These strains contain defined mutations within specific serotypes of bacteria. The invention also includes the use of these same mutational combinations contained within alternate serotypes or strains. Each of the mutations can be generated by chromosomal deletion techniques known to those skilled in the arts. Generally, the mutational combination includes at least two mutations. Such mutations are made sequentially and generally involve the elimination of antibiotic resistance markers. The process therefore consists of a first step in selection of an appropriate serotype based upon the known species specificity (e.g, S. typhi is human specific and S. typhimurium has broad species specificity including humans, birds, pigs and many other vertebrates). Thus, if the target species for immunization were limited to humans, S. typhi would be appropriate. If more species are desired to be immunized including humans, birds, pigs, dogs, horses and many other vertebrates, then other serotypes may be used. In a preferred embodiment, as S. typhimurium and S. montevidio which have non-overlapping O-antigen presentation (e.g., S. typhimurium is O-1,4,5,12 and S. typhi is Vi, S. montevideo is O-6,7) may be used. Thus, S. typhimurium is a suitable serotype for a prime/boost strategy where S. typhimurium is either the primary vaccine, or the booster vaccine where the primary vaccine is another serotype such as S. typhi or S. montevideo. Furthermore, S. typhimurium is suitable for humans, pigs or birds. A second step follows serotype selection where the first genetic mutation is introduced which may involve the use of antibiotic resistance markers and where any antibiotic resistance makers are then eliminated, followed by a third step where a second genetic mutation is introduced which may involve the use of antibiotic resistance markers and where any antibiotic resistance makers are then also eliminated. Reiteration of genetic deletion and antibiotic marker elimination can be used to supply additional mutations. Methods for reiterative chromosomal deletion and elimination of antibiotic resistance markers are known to those skilled in the arts, including TN10 transposon deletion followed by Bochner selection for elimination of the tetracycline antibiotic resistance marker, lambda red recombinase deletion followed by flip recombinase elimination of the antibiotic resistance marker, and suicide vectors such as those containing sucrase gene (e.g., pCVD442, Donnenberg and Kaper, 1991). By way of example, the pCVD442 vector is used in the following manner to create specific genetic deletions. First, the desired bacterial serotype is selected, such as Salmonella typhimurium. Second, the desired genetic background to be utilized is selected, such as AroA-, AroD-, htrA- which has been shown to be a safe mutational combination. The genes are then deleted in sequence using the pCVD442 vector as described by Donnenberg and Kaper 1991. The construction of the deletion vector uses DNA sequence for the gene of interest and/or the flanking 5' and 3' DNA. Such DNA may be known and previously deposited in a database, or new sequence obtained by methods known to those skilled in the arts such as low stringency hybridization. The isolation genes such as AroA, AroD, htrA or any other known attenuating mutation from Salmonella serotypes where the DNA sequence is not known is accomplished by low-stringency DNA/DNA hybridization of a Salmonella genomic DNA library carried in either E. coli or Salmonella LT2 5010 (e.g., Sambrook et al., 1989 Molecular Cloning: A laboratory manual ($2^{nd}$ Ed.), Cold Spring Harbor Laboratory Press; Low et al., 1999 Nature Biotechnology). A probe for the desired gene such as AroA, AroD, htrA or any other known attenuating mutation is generated from a known homologous gene and its corresponding DNA sequence of such as AroA, AroD, htrA or any other known attenuating mutation respectively, by PCR. This fragment is labeled using $^{32}$P-dCTP and used to probe the Salmonella library at low-stringency conditions consisting of 6× sodium chloride/sodium citrate (SSC), 0.1% sodium dodecyl sulfate (SDS), 2× Denhardts, 0.5% non-fat dry milk overnight at 55° C. Those skilled in the art will understand that higher or lower stringency can be achieved using variation in the 55° C. (higher temperature is a higher stringency used when excessive binding occurs) combined with higher or lower SSC concentration (lower buffer concentration is higher stringency used when excessive binding occurs; higher concentration is lower stringency used when insufficient binding occurs to generate a signal). Strongly hybridizing colonies are purified, and plasmids extracted and subjected DNA sequencing. DNA sequence flanking novel homologue is used to generate the 5' and 3' regions of a sucrase vector which can then be used to specifically delete that genetic element.

Flanking DNA representing 5' and 3' regions is then cloned into the sucrase vector using standard techniques such that the unification of these regions represents a genetic deletion within the desired gene of at least one nucleotide. Preferably, most or all of entire gene is deleted (See FIG. 8). The vector is transformed to the desired strain and selected for antibiotic (ampicillin) resistance. The ampicillin resistance is then eliminated by selection of deletion of the sucrase gene by plating the bacteria to agar plates containing sucrase as described by Donnenberg and Kaper, 1991. Reiteration of these steps targeted at additional genes results in multiple mutations within the desired genetic background.

2.2 Example of Generation of Novel Mutational Combinations.

Strains useful in the invention also include novel combinations of mutations including phoP, phoQ, cdt, cya, crp, poxA, rpoS, htrA, nuoG, pmi, pabA, pts, damA, purA, purB, purI, zwf, aroA, aroC, aroD, gua, cadA, rfc, rjb, rfa, ompR, msbB and the Suwwan deletion. Novel combinations are selected by experimental analysis of two factors, attenuation and immunogenicity. Attenuation, where the $LD_{50}$ by administration in normal immunocompetent mice (e.g., CD1) is greater than $10^5$, but not more than $10^9$, and/or the $LD_{50}$ by IV injection is more than $10^4$ but not more than $10^8$ is desirable, since this is expected to translate into a dose in humans which will neither be too potent and prone to potential overdosing and/or side effects, nor over-attenuated which would result in use of very large doses necessitating vastly greater manufacturing capability. A safe dose ($LD_0$) is first determined in mice, and may be extrapolated to other species on a per weight basis or on a basis of surface area (e.g., meters$^2$). A safe dose is the non-lethal dose determined by a toxicity study using standard methods (Welkos and O'Brian Taylor et al., Proc. Natl. Acad. Sci. USA 84: 2833-2837). In non-experimental animals including humans, a dose 1:100 or 1:1000 of the $LD_0$ may first be tested and then escalated to a maximum tolerated dose (MTD) defined as the maximum dose having acceptable toxicities which are not life threatening. A dose below or up to the MTD may be used. Immunogenicity is determined by methods know to those skilled in the art including wild type strain challenge and/or analysis for immune response to specific antigens, e.g., ELISA for LPS (e.g., FLOCKTYPE® Labor Diagnostik, Leipzig, Germany) or to the genetically engineered antigens as described further in examples 2.15 and 2.16. Strains which fall into the attenuation range and have the comparatively highest immune response as determined by ELISA and wild type immune challenge using methods known to those skilled in the arts are preferred. By way of example, the following three combinations are generated 1) aroA and purI, 2) aroA and Suwwan, and 3) aroA, purI and Suwwan are generated. DNA sequences for aroA and purI are known for *S. typhimurium.* The Suwwan deletion is described by Murray et al., 2004. The Suwwan deletion is selected for in ATCC strain 14028 using agar plates containing chlorate. Approximately one in three resistant stains contain the Suwwan deletion, which is confirmed by PCR using primers outside of the two IS200 elements (FIG. 8). The introduction of the Suwwan deletion is not followed by restoring antibiotic sensitivity, since chlorate is not clinically relevant and there is no antibiotic resistance gene inserted in the process. Thus, using the methods described by Donnenberg and Kaper 1991 as described in Example 2.1 and the derivation of the Suwwan deletion, the combined three mutations are generated: 1) aroA and purI, 2) aroA and Suwwan, and 3) aroA, purI and Suwwan. These combinations are then determined for $LD_{50}$ using standard methods (Welkos and O'Brian Taylor et al., Proc. Natl. Acad. Sci. USA 84: 2833-2837) and those with the desired attenuation profile described above are selected for further analysis. In a wild type challenge experiment, the mice are first administered the individual bacterial strain orally at a safe dose (i.e., an $LD_0$ or less than the $LD_{10}$ as defined from the same $LD_{50}$ experiment previously performed). Sublethal doses of the attenuated strains are expected to immunize the mice against the lethal wild type strain. At a suitable time period (for example, 2 to 6 weeks, 1 to 12 weeks, or 1 to 53 weeks) following a single administration of a dose less than the $LD_{10}$, either a booster dose also less than the $LD_{10}$ may be administered and staged for two additional weeks, or the challenge experiment may be performed. The challenge is performed in the form of an oral administration of a lethal dose of the wild type, usually 10 colony forming units (CFU) or greater, and a survival is monitored over time. Strains with the greatest immunization potential result in immunized mice with the longest survival. Immunization can also be determined by immune response to *Salmonella* antigens, such as the O-antigens, H-antigens or LPS. A determination of anti-LPS is performed using a commercially available ELISA kit. Bacterial strains with the appropriate attenuation and highest level of demonstrated immunization are used for vaccine carriers.

2.3 Example of Construction of the Suwwan Deletion in Strains Lacking the 17.7 IS200 Element.

The method for selection of the Suwwan deletion has been described by Murray et al., 2004 for the *Salmonella typhimurium* strain ATCC 14028. Since other *Salmonella* strains lack the additional IS200 element at Cs. 17.7, they do not undergo this specific chromosomal deletion. The invention further provides a method to allow the Suwwan deletion to occur in other *Salmonella* strains, by using a sucrase deletion construct as described above which contains the 3' and 5' flanking regions which occur in other strains, isolated using analogous primers and providing a multiple cloning site. The IS200 Cs 17.7 is then cloned by PCR into the multiple cloning site of the sucrase vector containing the flanking sequence of the empty IS200 site. Subsequent homologous recombination results in the addition of the IS200 to the site where it was previously absent. Subsequent selection for the Suwwan deletion is then performed, resulting in a strain with the analogous Cs 17 Cs 19 deletion.

2.4 Example of Construction of Synthetic, Codon Optimized Hemagglutinin Genes for Bacterial in a Cytosolic Form in *Salmonella.*

Codon optimized genes generated by reverse translation (a.k.a., back-translation) of the Avian *Influenza* genes or their highly pathogenic derivatives using *Salmonella* optimized codons and the synthetic gene constructed by annealing overlapping plus and minus strand oligonucleotides.

For cytoplasmic expression, a second codon GCT is added following the ATG start site, the two codons together with an upstream CC constitute the restriction endonuclease site NcoI (CCATGG). Following the final codon TGA, the restriction endonuclease site HindIII has been added, thus, a nucleic acid containing this sequence can be restriction digested with NcoI and HindIII and cloned into the NcoI/HindIII sites of the bacterial expression plasmid trc99a (Pharmacia/Upjohn). For convenience, the trc99a vector is modified to remove the sphI and pstI sites and addition of NotI and PacI sites (FIG. 1). This allow, for example, directional subcloning of the expression cassette consisting of the trc promoter and its ribosomal binding site, any given cloned gene within the multiple cloning site, and the downstream ribosomal RNA termination signals. SphI and PstI are removed from trc99a by restriction digestion with PstI and HindIII, agarose gel analysis and gel purification of the restriction digested plasmid minus the small DNA seq cleaved by the restriction enzymes, and ligation of a synthetic oligonucleotide

SEQ ID NO: 001
AGCTTGCA.

Clones may be further confirmed by restriction endonuclease analysis or DNA sequencing. The NotI and PacI sites are added by inverse PCR, where the primers consist of INVNOTF1

SEQ ID NO: 002
5'-GATCGCGGCCGCTTAATTAACATTCAAATATGTATCCGCTCATGAG-3' and INVNOTR1

SEQ ID NO: 003
5'-GATCGCGGCCGCGTATTTAGAAAAATAAACAAAAAGAGTTTG-3'

The forward primer introduces the NotI and PacI sites, and the reverse primer provides a second NotI site. The linear PCR product is then restriction digested with NotI and self-ligated, and transformed to *E. coli*. Confirmation of the correct clones is obtained by restriction analysis, where the isolated plasmids now contain NotI and PacI sites or by DNA sequencing.

Bacterial expression is tested by any applicable technique known to those skilled in the arts such as ELISA or immunoblot. Such plasmid can be transferred to a suitable *Salmonella* strain by standard transformation techniques to comprise a *Salmonella* strain which expresses the H5 antigen cytoplasmically and is capable of eliciting an immune response.

TABLE 1

*Salmonella typhimurium* LT2 [gbbct]: 4696 CDS's (1477317 codons)
fields: [frequency: per thousand] ([number])

| | | | |
|---|---|---|---|
| UUU 23.3 (34407) | UCU 7.2 (10665) | UAU 17.1 (25288) | UGU 4.8 (7154) |
| UUC 15.3 (22562) | UCC 10.1 (14953) | UAC 11.6 (17079) | UGC 6.6 (9817) |
| UUA 13.2 (19499) | UCA 6.2 (9186) | UAA 1.9 (2781) | UGA 1.0 (1466) |
| UUG 12.4 (18352) | UCG 9.5 (14062) | UAG 0.3 (452) | UGG 15.2 (22479) |
| CUU 11.8 (17442) | CCU 7.2 (10564) | CAU 13.3 (19643) | CGU 18.8 (27700) |
| CUC 10.4 (15425) | CCC 6.9 (10235) | CAC 9.6 (14171) | CGC 23.3 (34474) |
| CUA 4.9 (7257) | CCA 5.8 (8501) | CAA 12.7 (18796) | CGA 3.6 (5268) |
| CUG 53.6 (79180) | CCG 24.7 (36447) | CAG 31.0 (45726) | CGG 6.9 (10266) |
| AUU 29.3 (43251) | ACU 6.7 (9935) | AAU 17.8 (26263) | AGU 7.3 (10831) |
| AUC 24.4 (36114) | ACC 23.3 (34480) | AAC 20.1 (29752) | AGC 17.4 (25762) |
| AUA 5.3 (7886) | ACA 5.8 (8515) | AAA 31.7 (46882) | AGA 2.3 (3451) |
| AUG 27.4 (40490) | ACG 18.8 (27756) | AAG 11.3 (16630) | AGG 1.6 (2422) |
| GUU 15.5 (22914) | GCU 12.8 (18891) | GAU 31.6 (46740) | GGU 17.4 (25643) |
| GUC 18.2 (26821) | GCC 29.1 (42983) | GAC 20.3 (30060) | GGC 35.3 (52100) |
| GUA 11.4 (16792) | GCA 13.0 (19160) | GAA 35.4 (52232) | GGA 8.7 (12841) |
| GUG 25.2 (37210) | GCG 42.5 (62843) | GAG 20.7 (30586) | GGG 12.0 (17784) |

Coding GC 53.36% 1st letter GC 59.34% 2nd letter GC 41.20% 3rd letter GC 59.53%

TABLE 2

*Salmonella typhi* [gbbct]: 397 CDS's (116164 codons)
fields: [frequency: per thousand] ([number])

| | | | |
|---|---|---|---|
| UUU 23.8 (2767) | UCU 11.8 (1372) | UAU 18.9 (2192) | UGU 6.3 (727) |
| UUC 15.5 (1804) | UCC 10.4 (1209) | UAC 13.2 (1538) | UGC 5.6 (652) |
| UUA 15.3 (1783) | UCA 14.3 (1656) | UAA 1.7 (193) | UGA 1.3 (155) |
| UUG 12.3 (1434) | UCG 9.6 (1119) | UAG 0.4 (49) | UGG 12.8 (1491) |
| CUU 15.8 (1834) | CCU 10.0 (1165) | CAU 11.4 (1319) | CGU 15.2 (1765) |
| CUC 10.7 (1247) | CCC 6.7 (783) | CAC 7.2 (839) | CGC 12.5 (1456) |
| CUA 6.5 (754) | CCA 8.7 (1012) | CAA 13.9 (1618) | CGA 6.3 (729) |
| CUG 35.4 (4110) | CCG 14.5 (1689) | CAG 27.4 (3183) | CGG 7.8 (908) |
| AUU 27.7 (3214) | ACU 14.2 (1647) | AAU 26.6 (3086) | AGU 12.6 (1467) |
| AUC 20.5 (2382) | ACC 20.5 (2377) | AAC 22.6 (2629) | AGC 16.5 (1921) |
| AUA 9.5 (1107) | ACA 13.5 (1568) | AAA 35.8 (4156) | AGA 5.7 (666) |
| AUG 26.1 (3037) | ACG 15.9 (1845) | AAG 17.1 (1989) | AGG 4.5 (520) |
| GUU 20.1 (2339) | GCU 17.5 (2036) | GAU 34.0 (3947) | GGU 19.7 (2286) |
| GUC 15.6 (1817) | GCC 22.0 (2559) | GAC 20.1 (2332) | GGC 22.5 (2612) |
| GUA 12.8 (1484) | GCA 20.5 (2382) | GAA 35.1 (4080) | GGA 12.2 (1414) |
| GUG 19.6 (2274) | GCG 21.2 (2461) | GAG 21.1 (2446) | GGG 13.2 (1532) |

Coding GC 48.16% 1st letter GC 53.73% 2nd letter GC 40.62% 3rd letter GC 50.14%

A codon optimized sequence is generated by reverse or back translation, i.e., the conversion of the amino acid sequence into the appropriate DNA sequence. Because of redundancy of the genetic code, many amino acids have more than one possible codon set which will translate to the appropriate amino acid. Recognition sequences representations use the standard abbreviations (Eur. J. Biochem. 150: 1-5, 1985) to represent ambiguity.

R=G or A
Y=C or T
M=A or C
K=G or T
S=G or C
W=A or T
B=not A (C or G or T)
D=not C (A or G or T)
H=not G (A or C or T)
V=not T (A or C or G)
N=A or C or G or T Based upon the codon usage table which indicates preferences as higher percentages of usage and therefore optimal codons, a complete sequence can be back translated.

The H5 hemagglutinin gene has a number of known sequence, see e.g., Genbank LOCUS NC_007362, isolated from a goose in Guangdong, China in 1996, or a more preferably, a recent isolate such as CY019432, obtained from a 26-year old female human infected with avian *influenza* in Indonesia in 2006, expressly incorporated herein by reference.

The result of the reverse translation of CY019432 into a *Salmonella* codon optimized sequence is shown below (SEQ ID NO: 004).

```
GATCCCATGGCTGAGAAAATTGTGCTGCTGCTGTCCATTGTGTCGCTGGT

CAAAAGCGATCAGATCTGCATTGGCTACCATGCGAACAATAGCACCGAAC

AGGTTGATACCATTATGGAGAAAAACGTCACCGTGACCCATGCGCAGGAC

ATCCTGGAAAAAACCCATAATGGCAAACTGTGCGATCTGGATGGCGTCAA

ACCGCTGATCCTGAAAGATTGCAGCGTGGCGGGTTGGCTGCTGGGCAACC

CGATGTGCGATGAATTTATCAATGTTCCGGAATGGAGCTATATTGTGGAA

AAAGCGAATCCGACCAACGATCTGTGTTATCCGGGTTCGTTTAACGATTA

CGAAGAACTGAAACACCTGCTGAGCCGTATTAATCATTTTGAAAAAATCC

AGATTATTCCGAAATCGAGCTGGTCGGACCACGAGGCGAGCTCGGGCGTT

TCCTCCGCCTGCCCGTATCTGGGTAGCCCGAGCTTTTTTCGTAATGTGGT

CTGGCTGATCAAAAAAAATTCCACGTACCCGACCATTAAAAAAAGCTATA

ACAACACCAACCAGGAAGATCTGCTGGTGCTGTGGGGCATTCATCATCCG

AACAATGAAGAAGAACAGACCCGCCTGTACCAGAATCCGACCACCTATAT

TAGCATTGGCACCAGCACCCTGAATCAGCGTCTGGTTCCGAAAATTGCGA

CCCGCAGCAAAGTGAACGGCCAGTCCGGTCGTATGGAATTTTTTTGGACC

ATTCTGAAACCGAATGATGCCATCAACTTTGAATCCAATGGCAATTTTAT

CGCGCCGGAATACGCGTATAAAATCGTGAAAAAAGGCGATAGCGCCATTA

TGAAAAGCGAACTGGAATACTCCAACTGCAATACGAAATGTCAGACGCCG

ATGGGCGCGATCAACAGCTCGATGCCGTTTCACAACATCCATCCGCTGAC

CATTGGCGAGTGTCCGAAATATGTCAAAAGCAGCCGCCTGGTGCTGGCCA

CCGGCCTGCGCAATTCGCCGCAGCGTGAAAGCCGTCGCAAAAAACGTGGC

CTGTTTGGCGCGATTGCGGGCTTCATTGAAGGCGGCTGGCAGGGTATGGT

CGACGGCTGGTACGGTTATCATCATAGCAACGAACAGGGTAGCGGCTATG

CGGCGGATAAAGAATCCACCCAGAAAGCCATCGATGGTGTCACGAATAAA

GTGAATAGCATTATTGACAAAATGAACACCCAGTTCGAGGCGGTCGGCCG

CGAGTTTAATAATCTGGAACGCCGCATTGAAAATCTGAATAAAAAAATGG

AAGATGGCTTTCTGGACGTTTGGACCTATAACGCGGAACTGCTGGTCCTG

ATGGAGAACGAACGCACGCTGGACTTTCATGATTCCAACGTGAAAAATCT

GTACGATAAAGTTCGTCTGCAGCTGCGCGACAATGCCAAAGAACTGGGCA

ACGGCTGTTTCGAGTTTTATCATAAATGTGATAACGAATGCATGGAATCC

ATTCGTAACGGTACCTACAACTATCCGCAGTATAGCGAAGAAGCGCGCCT

GAAACGTGAAGAGATTTCGGGTGTGAAACTGGAATCCATTGGCACCTATC

AGATTCTGTCCATTTATAGCACCGTCGCCAGCTCCCTGGCCCTGGCCATT

ATGATTGCGGGCCTGAGCCTGTGGATGTGCTCCAACGGCTCCCTGCAGTG

TCGCATCTGCATCTGAAAGCTTGATC
```

The sequence begins with four spacer codons for restriction digestion and cloning. The Genbank sequence had a second codon inserted (GCT), which is a strong translational second codon in gram negative bacteria. The initiating codon ATG is underlined as well as the stop codon TGA which is followed by the nucleotides for the restriction site HindIII and four spacer codons.

2.5 Example of Construction of Synthetic, Codon Optimized Neuraminidase Genes for Bacterial in a Cytosolic Form in *Salmonella*.

Codon optimized N1 orf (SEQ ID NO: 005) is generated by reverse translation of the Avian *Influenza* gene using *Salmonella* optimized codons and the synthetic gene constructed by annealing overlapping plus and minus strand oligonucleotides as described in the example above. For cytoplasmic expression, a second codon GCT encoding alanine is added following the ATG start site encoding the initiating methionine, the two codons together with an upstream CC constitute the restriction endonuclease site NcoI. Further upstream the nucleotides GACT are added to increase the distance of the restriction site from the end, enhancing the abiligy of the enzyme to cut close to the end. Following the final amino acid codon a TGA stop codon, the restriction endonuclease site HindIII has been added, thus, a nucleic acid containing this sequence can be restriction digested with NcoI and HindIII and cloned into the NcoI/HindIII sites of the bacterial expression plasmid trc99a (Pharmacia/Upjohn). Bacterial expression is tested by any applicable technique known to those skilled in the arts such as ELISA or immunoblot. Such plasmids can be transferred to a suitable *Salmonella* strain by standard transformation techniques to comprise a *Salmonella* strain which expresses the H5 antigen cytoplasmically and when administered to an animal is capable of eliciting an immune response as described in example 7.15.

The N1 neuraminidase gene has a known sequence, see Genbank LOCUS NC_007361, expressly incorporated herein by reference.

Reverse translation using *Salmonella* codon preferences results in the following DNA sequence. (SEQ ID NO: 005)

```
GATC cc ATG (GCT)? AAT CCG AAC CAG AAA ATT ATC ACC
ATT GGC TCT ATT TGC ATG GTG GTA GGG ATC ATT TCC
CTG ATG TTA CAG ATC GGC AAC ATT ATC TCG ATC TGG
GTG TCC CAT TCT ATT CAG ACC GGC AAC CAG CAT CAG
GCC GAA CCG TGC AAT CAA AGC ATT ATC ACC TAC GAA
AAT AAC ACC TGG GTA AAT CAG ACC TAT GTT AAT ATT
TCA AAC ACC AAC TTC CTG ACC GAA AAA GCG GTG GCA
AGT GTA ACC CTC GCC GGT AAC AGC TCG CTG TGT CCT
ATT TCT GGC TGG GCG GTA CAC AGC AAA GAT AAT GGC
ATT CGC ATC GGC TCT AAA GGC GAC GTT TTT GTG ATC
CGC GAA CCC TTT ATT TCG TGT AGC CAT CTG GAG TGC
CGT ACC TTT TTC TTG ACC CAG GGG GCG CTG CTT AAC
GAT AAG CAT TCG AAT GGC ACG GTT AAA GAT CGC AGT
CCG CAC CGC ACG CTG ATG AGC TGC CCA GTG GGG GAG
GCC CCA TCC CCA TAC AAC TCG CGC TTC GAA TCC GTC
GCT TGG AGC GCC AGC GCG TGC CAC GAT GGT ACG TCT
TGG CTG ACG ATC GGC ATT AGC GGT CCG GAC AAC GGT
GCG GTT GCT GTC CTG AAA TAT AAT GGT ATT ATC ACG
GAC ACC ATT AAA TCG TGG CGC AAC AAT ATC TTA CGG
ACC CAG GAG TCA GAA TGC GCC TGC GTG AAT GGC TCT
TGC TTT ACG GTC ATG ACC GAT GGC CCG AGT AAT GGC
CAA GCG TCC TAT AAA ATT TTT AAA ATG GAA AAA GGG
AAA GTT GTG AAG TCA GTG GAA CTT AAC GCC CCG AAC
TAT CAC TAT GAA GAG TGT TCG TGT TAC CCT GAC GCA
GGC GAA ATC ACG TGT GTC TGC CGT GAT AAC TGG CAT
GGC AGC AAC CGC CCG TGG GTG TCC TTT AAC CAG AAT
TTG GAA TAT CAG ATC GGC TAT ATT TGT TCT GGG GTC
TTC GGC GAT AAC CCG CGT CCT AAT GAC GGC ACC GGC
AGC TGT GGC CCG GTA TCC CCC AAT GGT GCG TAT GGC
GTT AAG GGT TTC AGT TTC AAA TAC GGT AAT GGC GTG
TGG ATT GGT CGC ACC AAA TCA ACC AAC TCG CGG TCG
GGT TTT GAA ATG ATC TGG GAT CCG AAT GGC TGG ACC
GGT ACC GAT AGC TCA TTC TCC GTG AAG CAA GAC ATC
GTC GCA ATT ACG GAT TGG TCC GGC TAC AGT GGC AGC
TTT GTG CAA CAT CCG GAG CTG ACC GGG CTG GAT TGC
ATT CGC CCC TGT TTT TGG GTT GAA CTG ATT CGT GGG
CGT CCG AAG GAG TCA ACG ATC TGG ACG AGC GGC AGC
AGT ATT AGC TTT TGC GGC GTC AAC AGC GAC ACG GTC
GGC TGG AGT TGG CCG GAT GAC GCG GAG CTC CCT TTT
ACC ATT GAT AAA TAG AAG CTT GAT C
```

The sequence is further optimized for bacterial expression by addition of the appropriate restriction sites for cloning.

An NcoI site is engineered using the start codon together with second codon GCT and a stop codon is added after the final amino acid codon together with an engineered HindIII site and end spacer. Such a synthetically derived DNA sequence can then be cloned into the NcoI/HindIII sites of the bacterial expression plasmid pTrc99a and transformed into the *Salmonella* strain to result in a vaccine strain expressing the viral antigen.

2.6 Example of Construction of Synthetic, Codon Optimized Genes with Unique Restriction Endonuclease Sites for Rapidly Matching an Emerging Pathogen.

Oseltamivir-resistant neuraminidase is an example of an antigen with an altered amino acid sequence which could change antigenicity. The above synthetic construct in Example 2.5 above which contains restriction sites is further modified, where the synthetic sequence contains mutations representing resistance to oseltamivir, such as the histidine to tyrosine mutation at amino acid position 274 (H274Y). First the trc99a N1 expression construct is restriction endonuclease digested with appropriate sequences. A synthetic DNA construct containing the N1 sequence bearing the H274Y variation is obtained through synthetic construction and ligated into the restriction endonuclease target sites of the previously prepared gene. The plasmid is transfected into a suitable bacterial vector. Thus, the new construct is more rapidly generated and when expressed in the bacterial vector, results in a vaccine antigenically matched to the emerging oseltamivir resistant strain.

2.7 Example of Secretion of Avian *Influenza* Antigens and Highly Pathogenic Derivatives using HlyA fusion.

Avian *influenza* antigen polypeptides expressed from antigen-expressing plasmids or chromosomal constructs in the vaccine strains described herein need not be linked to a signal peptide or other peptide for membrane localization or secretion across the cell membrane. However, by way of further example of a preferred embodiment, a nucleotide sequence that encodes an H5-HlyA fusion polypeptide useful in the invention is known in the art, and the corresponding encoded H5-HlyA fusion polypeptide has the corresponding amino acid sequence. The antigen-expressing plasmids useful in the invention may be engineered to express an Avian *Influenza* antigen polypeptide intracellularly in a host *Salmonella* strain. Preferably, antigen-expressing plasmids or chromosomal expression constructs useful in the invention are engineered to express secreted forms of Avian *Influenza* antigen polypeptide extracellularly. Accordingly, Avian *Influenza* antigen polypeptides expressed from antigen-expressing plasmids in the vaccine strains described herein, are preferably linked to a signal peptide or other peptide for membrane localization or secretion across the cell membrane.

Construction of hemolysin A (hlyA) fusions with H5 nucleotide sequence to result in an hlyA secreted fusion peptide. HlyA fusions are generated using plasmids that provide the 60 C terminal amino acids of HLYA [(Gentschev, et al., 1994. Synthesis and secretion of bacterial antigens by attenuated *Salmonella* via the *Escherichia coli* hemolysin secretion system. Behring Inst. Mitt. 95:57-66; Holland et al. U.S. Pat. No. 5,143,830) by methods known to those skilled in the arts and ligated into the hlyA fusion vector to generate a nucleic acid sequence encoding an H5:HLYA fusion peptide. The fusion may also be generated as a completely synthetic DNA construct as described for the hemagglutinin and neuraminidase genes.

An example of the CY019432 codon optimized H5 gene operably fused to the 60 C-terminal amino acids of HlyA is shown below. (SEQ ID NO: 006)

GATCCC<u>AT</u>GGCTGAGAAAATTGTGCTGCTGCTGTCCATTGTGTCGCTGGT

CAAAAGCGATCAGATCTGCATTGGCTACCATGCGAACAATAGCACCGAAC

AGGTTGATACCATTATGGAGAAAAACGTCACCGTGACCCATGCGCAGGAC

ATCCTGGAAAAAACCCATAATGGCAAACTGTGCGATCTGGATGGCGTCAA

ACCGCTGATCCTGAAAGATTGCAGCGTGGCGGGTTGGCTGCTGGGCAACC

CGATGTGCGATGAATTTATCAATGTTCCGGAATGGAGCTATATTGTGGAA

AAAGCGAATCCGACCAACGATCTGTGTTATCCGGGTTCGTTTAACGATTA

CGAAGAACTGAAACACCTGCTGAGCCGTATTAATCATTTTGAAAAAATCC

AGATTATTCCGAAATCGAGCTGGTCGGACCACGAGGCGAGCTCGGGCGTT

TCCTCCGCCTGCCCGTATCTGGGTAGCCCGAGCTTTTTTCGTAATGTGGT

CTGGCTGATCAAAAAAAATTCCACGTACCCGACCATTAAAAAAAGCTATA

ACAACACCAACCAGGAAGATCTGCTGGTGCTGTGGGGCATTCATCATCCG

AACAATGAAGAAGAACAGACCCGCCTGTACCAGAATCCGACCACCTATAT

TAGCATTGGCACCAGCACCCTGAATCAGCGTCTGGTTCCGAAAATTGCGA

CCCGCAGCAAAGTGAACGGCCAGTCCGGTCGTATGGAATTTTTTTGGACC

ATTCTGAAACCGAATGATGCCATCAACTTTGAATCCAATGGCAATTTTAT

CGCGCCGGAATACGCGTATAAAATCGTGAAAAAAGGCGATAGCGCCATTA

TGAAAAGCGAACTGGAATACTCCAACTGCAATACGAAATGTCAGACGCCG

ATGGGCGCGATCAACAGCTCGATGCCGTTTCACAACATCCATCCGCTGAC

CATTGGCGAGTGTCCGAAATATGTCAAAAGCAGCCGCCTGGTGCTGGCCA

CCGGCCTGCGCAATTCGCCGCAGCGTGAAAGCCGTCGCAAAAAACGTGGC

CTGTTTGGCGCGATTGCGGGCTTCATTGAAGGCGGCTGGCAGGGTATGGT

CGACGGCTGGTACGGTTATCATCATAGCAACGAACAGGGTAGCGGCTATG

CGGCGGATAAAGAATCCACCCAGAAAGCCATCGATGGTGTCACGAATAAA

GTGAATAGCATTATTGACAAAATGAACACCCAGTTCGAGGCGGTCGGCCG

CGAGTTTAATAATCTGGAACGCCGCATTGAAAATCTGAATAAAAAAATGG

AAGATGGCTTTCTGGACGTTTGGACCTATAACGCGGAACTGCTGGTCCTG

ATGGAGAACGAACGCACGCTGGACTTTCATGATTCCAACGTGAAAAATCT

GTACGATAAAGTTCGTCTGCAGCTGCGCGACAATGCCAAAGAACTGGGCA

ACGGCTGTTTCGAGTTTTATCATAAATGTGATAACGAATGCATGGAATCC

ATTCGTAACGGTACCTACAACTATCCGCAGTATAGCGAAGAAGCGCGCCT

GAAACGTGAAGAGATTTCGGGTGTGAAACTGGAATCCATTGGCACCTATC

AGATTCTGTCCATTTATAGCACCGTCGCCAGCTCCCTGGCCCTGGCCATT

ATGATTGCGGGCCTGAGCCTGTGGATGTGCTCCAACGGCTCCCTGCAGTG

TCGCATCTGCATCCCCGGGTCAACTTATGGGAGCCAGGACTATCTTAATC

CATTGATTAATGAAATCAGCAAAATCATTTCAGCTGCAGGTAATTTGGAT

-continued

GTTAAGGAGGAAAGATCTGCCGCTTCTTTATTGCAGTTGTCCGGTAATGC

CAGTGATTTTTCATATGGACGGAACTCAATAACTTTGACAGCATCAGCA<u>T</u>

<u>AAAAGCTTGATC</u>

The sequence begins with four spacer codons for restriction digestion and cloning. The Genbank sequence had a second codon inserted (GCT) in the H5 gene, which is a strong translational second codon in gram negative bacteria. The initiating codon ATG is underlined. A SmaI restriction endonuclease site has been added in place of the H5 stop codon to facilitate cloning and the fusion of the peptides, followed by in-frame coding sequence for the 60 C-terminal amino acids of the HlyA gene, which ends with the stop codon TAA (underlined) which is followed by the nucleotides for the restriction site HindIII and four spacer codons. A naturally occurring PacI restriction endonuclease site occurring within HlyA has been conservatively altered to facilitate the potential use of PacI as a restriction site outside of the coding sequence.

The secretion of the hlyA fusion requires the presence of the HlyBD gene products. In order to provide for the presence of the HlyBD genes, a plasmid containing the genes may be used (FIG. 4), or preferably, the HlyBD genes are cloned within a sucrase vector such as an IS200 phage recombinase, flagellar, or hin pCVD deletion vector. The entire export cassette can be excised from pVDL9.3 as a NotI-digested fragment and cloned into the NotI site of a sucrase vector, which when recombined with the chromosome, results in deletion of the IS200 phage recombinase, flagellar, or Hin and insertion of the HlyBD genes into the chromosome.

2.8 Example of Secretion of Avian *Influenza* Antigens and Highly Pathogenic Derivatives using ClyA fusion.

Construction of clyA fusions with hemagglutinin and neuraminidase antigens are generate according to the methods of Galen et al. (2004 Infection and Immunity 72: 7096-7106).

2.9 Example of Secretion of Avian *Influenza* Antigens and Highly Pathogenic Derivatives using Autotransporter Fusions.

Construction of autotransporter fusions with hemagglutinin and neuraminidase antigens. Autotransporter chimeric proteins are capable of self-transportation/secretion outside the bacterial cell. Hemagglutinin and neuraminidase fusions with the IgA protease autotransporter protein of *Neisseria gonorrhoeae* are constructed according to the methods of Veiga et al., 2003 J. Virol. 2003 77: 13396-13398) and Oomen et al., 2004 EMBO Journal 23: 1257-1266. The resulting fusion construct, when transfected into a bacterial vector, results in a vaccine strain which secretes the neuraminidase and hemagglutinin antigens.

2.10 Example of Secretion of Avian *Influenza* Antigens and Highly Pathogenic Derivatives using Colicin E3 Fusions.

Colicin E3 (ColE3) is a bacterial ribosomal RNA inactivating toxin. ColE3 is neutralized within the cells that express it by an antitoxin which inhibits is anti-ribosomal activity. An inactivated ColE3 is cloned from a colE3 containing bacterial strain (e.g., ColE3-CA38). PCR primers consist of a forward primer which clones the start codon with a second added codon and providing an NcoI cloning site and a reverse primer which contains a SmaI (blunt end) cloning site. The PCR primer is situated sufficiently far down the sequence, such that the C-terminal portion of the protein is absent, thus inactivating the toxic activity while retaining the secretion activity. The hemagglutinin and neuraminidase antigens are cut with NcoI and HindIII, blunt end polished and ligated in-frame into the SmaI site of the truncated ColE3 protein. The DNA orientation is then confirmed by restriction analysis and DNA sequencing. When transformed into the bacterial vector, the DNA construct results in secreted hemagglutinin or neuraminidase antigens.

2.11 Example of Genetic Stabilization by Deletion of IS200 Elements.

Using the generalized pCVD442 method homologous recombination technique using the vector pCVD442 (Donnenberg and Kaper, 1991), IS200 elements can be deleted. Such elements in the *Salmonella typhimurium* strain LT2 includes LOCUS NC_003197, having a sequence well known in the art. The IS200 elements contain a transposase with a well known amino acid sequence.

Additional IS200 elements, if not known by DNA sequence, can be isolated by low stringency hybridization. The isolation IS200 elements from *Salmonella* by low-stringency DNA/DNA hybridization of a *Salmonella* genomic DNA library carried in *Salmonella* LT2 5010 (e.g., Low et al., 1999 Nature Biotechnology). A probe for IS200 is generated from a known IS200 element by PCR. This fragment is labeled using $^{32}$P-dCTP and used to probe the *Salmonella* library at low-stringency conditions consisting of 6× sodium chloride/sodium citrate (SSC), 0.1% sodium dodecyl sulfate (SDS), 2× Denhardts, 0.5% non-fat dry milk overnight at 55° C. Strongly hybridizing colonies are purified, and plasmids extracted and subjected DNA sequencing. DNA sequence flanking novel IS200 elements is used to generate the 5' and 3' regions of a sucrase vector which can then be used to specifically delete that IS200 element.

By way of specific example, the IS200 located in 17.7 Cs. can be deleted using a 5' section generated using the PCR primers 2415F1 (IS200 5'F with SacI)

SEQ ID NO: 007
GATCGAGCTCGGCTTAATTATTGCCCAGCTTGCGCTGG and 2415R1 (IS200 5'R with poly linker)

SEQ ID NO: 008
CCCCGCATGCGGGGCTCGAGGGGGCCATATAGGCCGGGGATTTAAATGGG

GCGGCCGCAAAAAAAATCCTGGCGCAGGGCCAGG and a 3' section using the primers 2413F1 (IS200 3'F with poly)

SEQ ID NO: 009
CCCCGCATGCGGGGAGATCTGGGGTTAATTAAGGGGTCTAGAGGGGCGG

CCGCAGGACTATATTTAGGGCGAAACAGC and 2413R1 (IS200 3'R with SalI)

SEQ ID NO: 010
GATCGTCGACGACTAAACATGATTCCAACAATCACG.

The 5' section is cloned into the pCVD442 vector using SacI and SphI, and subsequently, after isolation and identification of the appropriate clone, the 3' section is added using the restriction endonuclease enzymes SphI and SalI. The primers also provide a multiple cloning site containing Not1, Pac1, BstY1, Sph1, Sfi1, Swa1, which can be used to deliver exogenous genes such as the H5 and N1, the lambda repressor C1, or the hlyBD (protein channel) described further below.

2.12 Example of Genetic Stabilization by Deletion of Phage Elements.

Bacterial strains containing phage or prophage elements may have the phage enter a lytic cycle in which they may undergo recombination inversion. Bacterial strains such as *Salmonella* contain Fels and Gifsy prophage. The Fels prophage recombinase/invertases can be deleted using the pCVD442 homologous recombination system as described above for IS200 elements. Deletion results in the inability to excise the phage DNA and therefore is unable to undergo the lytic cycle or genetic recombination.

The Fels-1 invertase has a well known amino acid and DNA sequence. The Fels-2 recombinase/invertases also have known amino acid sequences, and DNA sequences.

2.13 Example of Genetic Isolation by Constitutive Expression of the P22 Phage C2 Repressor.

See: Donnenberg and Kaper, 1991; Low et al. (Methods in Molecular Medicine, 2003), expressly incorporated herein by reference.

2.14 Example of Chromosomal Integration of a Synthetically Constructed avian *Influenza* Hemagglutinin Gene and Neuraminidase gene.

See: Donnenberg and Kaper, 1991; Low et al. (Methods in Molecular Medicine, 2003), expressly incorporated herein by reference.

2.15 Example of Determining Immune Response to H5N1 Expressing Bacteria.

Experimental determination of vaccine activity is known to those skilled in the art. By way of non-limiting example, determination of an antibody response is demonstrated.

1) Vertebrate animals including mice, birds, dogs, cats, horses, pigs or humans are selected for not having any known current or recent (within 1 year) *influenza* infection or vaccination. Said animals are pre-bled to determine background binding to, for example, H5 and N1 antigens.
2) The *Salmonella* expressing H5 and N1 are cultured on LB agar overnight at 37°. Bacteria expressing other H and or N antigens may also be used.
3) The following day the bacteria are transferred to LB broth, adjusted in concentration to $OD_{600}$=0.1 (~2×10$^8$ cfu/ml), and subjected to further growth at 37° on a rotator to $OD_{600}$=2.0, and placed on ice, where the concentration corresponds to approx. 4×10$^9$ cfu/ml.
4) Following growth, centrifuged and re-suspended in 1/10 the original volume in a pharmacologically suitable buffer such as PBS and they are diluted to a concentration of 10$^4$ to 10$^9$ cfu/ml in a pharmacologically suitable buffer on ice, warmed to room temperature and administered orally or intranasally in a volume appropriate for the size of the animal in question, for example 50 µl for a mouse or 10 to 100 ml for a human. The actual dose measured in total cfu is determined by the safe dose as described elsewhere in this application.
5) After 2 weeks, a blood sample is taken for comparison to the pretreatment sample. A booster dose may be given. The booster may be the same as the initial administration, a different species, a different serotype, or a different flagellar antigen (H1 or H2) or no flagellar antigen.
6) After an additional 2 to 4 weeks, an additional blood sample may be taken for further comparison with the pretreatment and 2-week post treatment.

7) A comparison of preimmune and post immune antibody response is preformed by immunoblot or ELISA. A positive response is indicated by a relative numerical value 2× greater then background/preimmune assay.

2.16 Example of Immunization with H5N1 Bacterial Vaccine Strains.

An experiment to determine if H5N1 strains of *Salmonella* are capable of providing protection from challenge with the wildtype strain. Ducks are immunized orally with 5×10$^9$ cfu of bacteria when 4 weeks old, then challenged with the standard challenge model of avian *influenza* at 6 weeks age.

Birds in Group A are immunized with empty vector. Group B receive *Salmonella* H5N1. Group C is immunized with *Salmonella* expressing the Tamiflu resistant neuraminidase mutations.

Birds in Group D are not immunized. Each group is further divided into +/− Tamiflu treatment. Results of these experiments can be used to demonstrate the effectiveness of the vaccine on Tamiflu resistant strain, with and without Tamiflu treatment.

Other Embodiments

Other embodiments are within the claims set forth below. For example, the host bacterium (the bacterium the chromosome of which is engineered to encode a heterologous antigen) can be *E. coli* or any other enteric bacterium, including *Salmonella, Bordetella, Shigella, Yersinia, Citrobacter, Enterobacter, Klebsiella, Morganella, Proteus, Providencia, Serratia, Plesiomonas,* and *Aeromonas,* all of which are known or believed to similar to the promoters of *E. coli* and *Salmonella*. Also potentially useful would be a bacille Calmette-Guerin (BCG) vaccine strain engineered to encode a heterologous antigen. The promoter used can be native to the species of the host bacterium, or can be a heterologous promoter (i.e., from a species other than that of the host bacterium) engineered into the host bacterium along with the heterologous antigen coding sequence, using standard genetic engineering techniques. Multiple heterologous antigen coding sequences linked to the same or different promoter sequences can be inserted into a given chromosome, using techniques analogous to those set forth above, to produce a multivalent vaccine strain.

Those who practice in the field of prokaryotic gene expression will realize that, while naturally-occurring promoter sequences are preferred, synthetic sequences or a hybrid of two or more sequences would also be expected to be useful in the chromosomes of the invention. Alteration, addition or deletion of one or a few nucleotides within a naturally-occurring promoter sequence would generally not affect its usefulness. The invention therefore encompasses promoters having such inconsequential changes.

What is claimed is:

1. A live genetically engineered bacterium, comprising:
a genetically engineered chromosomally integrated DNA construct which is stabilized against transduction of other bacteria, having a prokaryotic promoter sequence and encoding for production within the live genetically engineered bacterium of a fusion peptide comprising a bacterial secretion signal peptide portion and an immunogenic polypeptide portion; and
said live genetically engineered bacterium having a secretion mechanism which interacts with at least the bacterial secretion signal peptide portion to cause extracellular secretion of the fusion peptide across a cell membrane of the live genetically engineered bacterium; and
at least one bacterial chromosomal genetic virulence attenuating mutation to limit the live genetically engineered bacterium to cause non-persistent, non-systemic, and non-lethal infection of a tissue within a human or animal,
the live genetically engineered bacterium being adapted to induce a sufficient immune response to the immunogenic polypeptide portion to provide the human or animal an efficacious therapeutic or preventive vaccine.

2. The live genetically engineered bacterium according to claim 1, wherein the genetically engineered DNA construct is integrated into a chromosome of the live genetically engineered bacteria, further comprising deletions in bacteria phage or prophage elements.

3. The live genetically engineered bacterium according to claim 1, wherein the genetically engineered DNA construct is integrated into a chromosome of the live genetically engineered bacteria, further comprising at least one constitutively expressed phage repressor.

4. The live genetically engineered bacterium according to claim 1, wherein the genetically engineered DNA construct is integrated into a chromosome of the live genetically engineered bacteria, further comprising deletions in bacteria phage or prophage elements and at least one phage repressor which: (a) prevent phage excision, (b) prevent genetic rearrangement using phage or prophage elements, (c) prevent new infections by phage, and (d) prevent transduction by phage.

5. The live genetically engineered bacterium according to claim 1, wherein the live genetically engineered bacterium is adapted to selectively colonize the gut of a host human or animal, and to selectively secrete the fusion peptide within the gut of the host human or animal.

6. The live genetically engineered bacterium according to claim 1, wherein the immunogenic polypeptide portion comprises a prokaryotic-expression optimized peptide which corresponds to an antigen from a eukaryote.

7. The live genetically engineered bacterium according to claim 6, wherein the prokaryotic-expression optimized peptide is determined by back-translation of a peptide antigen from the eukaryote.

8. The live genetically engineered bacterium according to claim 1, wherein the prokaryotic promoter is selected from the group consisting of nirB, Plac, Ptac, Ptrc, PpagC, PpmrH, PpmrD, PompC, PnirB, PssrA, ProU, Pdps, and PssaG.

9. The live genetically engineered bacterium according to claim 1, wherein the bacterium is a *Salmonella* spp. selected from the group consisting of *Salmonella enterica* serovar *Typhimurium* (*S. typhimurium*), *Salmonella montevideo*, *Salmonella enterica* serovar *Typhi* (*S. typhi*), *Salmonella enterica* serovar *Paratyphi B* (*S. paratyphi B*), *Salmonella enterica* serovar *Paratyphi C* (*S. paratyphi C*), *Salmonella enterica* serovar *Hadar* (*S. hadar*), *Salmonella enterica* serovar *Enteriditis* (*S. enteriditis*), *Salmonella enterica* serovar *Kentucky* (*S. Kentucky*), *Salmonella enterica* serovar *Infantis* (*S. infantis*), *Salmonella enterica* serovar *Pullorum* (*S. pullorum*), *Salmonella enterica* serovar *Gallinarum* (*S. gallinarum*), *Salmonella enterica* serovar *Muenchen* (*S. muenchen*), *Salmonella enterica* serovar *Anaturn* (*S. anatum*), *Salmonella enterica* serovar *Dublin* (*S. Dublin*), *Salmonella enterica* serovar *Derby* (*S. derby*), *Salmonella enterica* serovar *Choleraesuis* var. *kunzendorf* (*S. cholerae kunzendorf*), and *Salmonella enterica* serovar *minnesota* (*S. Minnesota*).

10. The live genetically engineered bacterium according to claim 9, wherein the live genetically engineered bacterium is *S. enterica* serovar *Typhimurium* (*S. typhimurium*), genetically engineered to delete IS200 elements, and to constitutively express P22 phage C2 repressor.

11. The live genetically engineered bacterium according to claim 1, wherein the at least one genetic virulence attenuating mutation is in at least one genetic locus selected from the group consisting of phoP, phoQ, Mt, cya, crp, poxA, rpoS, htrA, nuoG, pmi, galE, pabA, pts, damA, purA, purB, purI, zwf, gua, cadA, rfic, rjb, rfa, ompR, msbB, and Suwwan.

12. The live genetically engineered bacteria according to claim 1, wherein the live genetically engineered bacterium is derived from *Salmonella typhimurium* ATCC 14028.

13. The live genetically engineered bacteria according to claim 1, wherein the live genetically engineered bacterium is derived from one of Ty21a, CMV906, CMV908, CMV906-htr, CMV908-htr, Ty800, holavax, MO1ZH09, and VNP20009.

14. The live genetically engineered bacteria according to claim 1, wherein the live genetically engineered bacterium is derived from *Salmonella typhimurium* ATCC 14028, with a Suwwan deletion.

15. The live genetically engineered bacteria according to claim 14, wherein the at least one genetic virulence attenuating mutation comprises a mutation of msbB.

16. The live genetically engineered bacteria according to claim 1, wherein the live genetically engineered bacterium secretes at least one of an fH1 antigen and an immunogenic portion of an fH1 antigen.

17. The live genetically engineered bacterium according to claim 1, further comprising a pharmaceutical formulation adapted for oral administration of a plurality of the live genetically engineered bacteria to a human, to induce a protective immune response to a virus or organism which produces an antigen corresponding to the immunogenic polypeptide portion.

18. A method of immunizing a human or animal, comprising administering the live genetically engineered bacterium in the pharmaceutical formulation according to claim 17 to the human or animal according to a prime/boost administration protocol, to achieve at least one of a protective and therapeutic response in the human or animal to the virus or organism.

19. A live genetically engineered bacterium, comprising:
a chromosomally-integrated genetically engineered DNA construct, which is stabilized against transduction of other bacteria, having a prokaryotic promoter sequence and encoding a fusion peptide for translation within the live genetically engineered bacterium, comprising a bacterial secretion signal peptide portion and an immunogenic polypeptide portion;
deletions in bacteria phage or prophage elements with respect to a wild type bacterium from which the live genetically engineered bacterium is derived;
a secretion mechanism which interacts with at least the bacterial secretion signal peptide portion, to cause a secretion of the fusion peptide from the live genetically engineered bacterium; and
at least one genetic virulence attenuating mutation with respect to a wild type bacterium from which the live genetically engineered bacterium is derived,
wherein the live genetically engineered bacterium is adapted to persist in a gut of a human or animal after oral administration thereof, to cause a therapeutic or preventative vaccination response to a virus or organism which is associated with the immunogenic polypeptide portion.

20. A live genetically engineered bacterium, comprising:
a bacterial chromosome, having a deletion of at least one genetically-destabilizing insertion sequence;
a constitutively expressed phage repressor;
at least one deletion of phage or prophage elements which enhance genetic stability with respect to transduction of other bacteria and to prevent phage excision;
a bacterial secretion mechanism, configured to interact with a peptide having a bacterial secretion signal peptide sequence portion, to secrete the peptide across a cell membrane of the live genetically engineered bacterium;
a genetically engineered DNA construct comprising a prokaryotic promoter sequence and an encoding sequence translatable into the peptide comprising a fusion of the bacterial secretion signal peptide portion configured to interact with the bacterial secretion mechanism, and an immunogenic polypeptide portion configured to interact with a host animal immune system to cause at least a humoral immune response; and
the live genetically engineered bacterium being non-virulent and adapted to cause non-lethal and non-persistent infection of a tissue within a human or animal, and being provided in a pharmaceutical formulation, to provide a therapeutic or preventive vaccine response of the host human or animal which is selectively based on the immunogenic polypeptide portion.

* * * * *

```
                           SEQUENCE LISTING

<160> NUMBER OF SEQ ID NOS: 10

<210> SEQ ID NO 1
<211> LENGTH: 8
<212> TYPE: DNA
<213> ORGANISM: Unknown
<220> FEATURE:
<223> OTHER INFORMATION: Synthetic Oligonucleotide

<400> SEQUENCE: 1 agcttgca                                                              8

<210> SEQ ID NO 2
<211> LENGTH: 46
<212> TYPE: DNA
<213> ORGANISM: Unknown
<220> FEATURE:
<223> OTHER INFORMATION: PCR Primer

<400> SEQUENCE: 2
gatcgcggcc gcttaattaa cattcaaata tgtatccgct catgag            46

<210> SEQ ID NO 3
<211> LENGTH: 42
<212> TYPE: DNA
<213> ORGANISM: Unknown
<220> FEATURE:
<223> OTHER INFORMATION: PCR Primer

<400> SEQUENCE: 3
gatcgcggcc gcgtatttag aaaaataaac aaaaagagtt tg                42

<210> SEQ ID NO 4
<211> LENGTH: 1726
<212> TYPE: DNA
<213> ORGANISM: Influenza A virus

<400> SEQUENCE: 4
```

-continued

```
gatcccatgg ctgagaaaat tgtgctgctg ctgtccattg tgtcgctggt caaaagcgat     60
cagatctgca ttggctacca tgcgaacaat agcaccgaac aggttgatac cattatggag    120
aaaaacgtca ccgtgaccca tgcgcaggac atcctggaaa aaacccataa tggcaaactg    180
tgcgatctgg atggcgtcaa accgctgatc ctgaaagatt gcagcgtggc gggttggctg    240
ctgggcaacc cgatgtgcga tgaatttatc aatgttccgg aatggagcta tattgtggaa    300
aaagcgaatc cgaccaacga tctgtgttat ccgggttcgt ttaacgatta cgaagaactg    360
aaacacctgc tgagccgtat taatcatttt gaaaaaatcc agattattcc gaaatcgagc    420
tggtcggacc acgaggcgag ctcgggcgtt tcctccgcct gcccgtatct gggtagcccg    480
agcttttttc gtaatgtggt ctggctgatc aaaaaaaatt ccacgtaccc gaccattaaa    540
aaaagctata acaacaccaa ccaggaagat ctgctggtgc tgtggggcat tcatcatccg    600
aacaatgaag aagaacagac ccgcctgtac cagaatccga ccacctatat tagcattggc    660
accagcaccc tgaatcagcg tctggttccg aaaattgcga cccgcagcaa agtgaacggc    720
cagtccggtc gtatggaatt tttttggacc attctgaaac cgaatgatgc catcaacttt    780
gaatccaatg gcaattttat cgcgccggaa tacgcgtata aaatcgtgaa aaaaggcgat    840
agcgccatta tgaaaagcga actggaatac tccaactgca atacgaaatg tcagacgccg    900
atgggcgcga tcaacagctc gatgccgttt cacaacatcc atccgctgac cattggcgag    960
tgtccgaaat atgtcaaaag cagccgcctg gtgctggcca ccggcctgcg caattcgccg   1020
cagcgtgaaa gccgtcgcaa aaaacgtggc ctgtttggcg cgattgcggg cttcattgaa   1080
ggcggctggc agggtatggt cgacggctgg tacggttatc atcatagcaa cgaacagggt   1140
agcggctatg cggcggataa agaatccacc cagaaagcca tcgatggtgt cacgaataaa   1200
gtgaatagca ttattgacaa aatgaacacc cagttcgagg cggtcggccg cgagtttaat   1260
aatctggaac gccgcattga aaatctgaat aaaaaaatgg aagatggctt tctggacgtt   1320
tggacctata acgcggaact gctggtcctg atggagaacg aacgcacgct ggactttcat   1380
gattccaacg tgaaaaatct gtacgataaa gttcgtctgc agctgcgcga caatgccaaa   1440
gaactgggca acggctgttt cgagttttat cataaatgtg ataacgaatg catggaatcc   1500
attcgtaacg gtacctacaa ctatccgcag tatagcgaag aagcgcgcct gaaacgtgaa   1560
gagatttcgg gtgtgaaact ggaatccatt ggcacctatc agattctgtc catttatagc   1620
accgtcgcca gctccctggc cctggccatt atgattgcgg gcctgagcct gtggatgtgc   1680
tccaacggct ccctgcagtg tcgcatctgc atctgaaagc ttgatc                  1726
```

<210> SEQ ID NO 5
<211> LENGTH: 1429
<212> TYPE: DNA
<213> ORGANISM: Influenza A virus

<400> SEQUENCE: 5

```
gatcccatgg ctaatccgaa ccagaaaatt atcaccattg gctctatttg catggtggta     60
gggatcattt ccctgatgtt acagatcggc aacattatct cgatctgggt gtcccattct    120
attcagaccg gcaaccagca tcaggccgaa ccgtgcaatc aaagcattat cacctacgaa    180
aataacacct gggtaaatca gacctatgtt aatatttcaa acaccaactt cctgaccgaa    240
aaagcggtgg caagtgtaac cctcgccggt aacagctcgc tgtgtcctat ttctggctgg    300
gcggtacaca gcaaagataa tggcattcgc atcggctcta aaggcgacgt tttgtgatc    360
cgcgaaccct ttatttcgtg tagccatctg gagtgccgta cctttttctt gacccagggg    420
```

```
gcgctgctta acgataagca ttcgaatggc acggttaaag atcgcagtcc gcaccgcacg    480
ctgatgagct gcccagtggg ggaggcccca tccccataca actcgcgctt cgaatccgtc    540
gcttggagcg ccagcgcgtg ccacgatggt acgtcttggc tgacgatcgg cattagcggt    600
ccggacaacg gtgcggttgc tgtcctgaaa tataatggta ttatcacgga caccattaaa    660
tcgtggcgca acaatatctt acggacccag gagtcagaat gcgcctgcgt gaatggctct    720
tgctttacgg tcatgaccga tggcccgagt aatggccaag cgtcctataa aatttttaaa    780
atggaaaaag ggaaagttgt gaagtcagtg gaacttaacg ccccgaacta tcactatgaa    840
gagtgttcgt gttaccctga cgcaggcgaa atcacgtgtg tctgccgtga taactggcat    900
ggcagcaacc gcccgtgggt gtcctttaac cagaatttgg aatatcagat cggctatatt    960
tgttctgggg tcttcggcga taacccgcgt cctaatgacg gcaccggcag ctgtggcccg   1020
gtatccccca atggtgcgta tggcgttaag ggtttcagtt tcaaatacgg taatggcgtg   1080
tggattggtc gcaccaaatc aaccaactcg cggtcgggtt ttgaaatgat ctgggatccg   1140
aatggctgga ccggtaccga tagctcattc tccgtgaagc aagacatcgt cgcaattacg   1200
gattggtccg gctacagtgg cagctttgtg caacatccgg agctgaccgg gctggattgc   1260
attcgcccct gtttttgggt tgaactgatt cgtgggcgtc cgaaggagtc aacgatctgg   1320
acgagcggca gcagtattag cttttgcggc gtcaacagcg acacggtcgg ctggagttgg   1380
ccggatgacg cggagctccc ttttaccatt gataaataga agcttgatc               1429
```

<210> SEQ ID NO 6
<211> LENGTH: 1912
<212> TYPE: DNA
<213> ORGANISM: Influenza A virus

<400> SEQUENCE: 6

```
gatcccatgg ctgagaaaat tgtgctgctg ctgtccattg tgtcgctggt caaaagcgat     60
cagatctgca ttggctacca tgcgaacaat agcaccgaac aggttgatac cattatggag    120
aaaaacgtca ccgtgaccca tgcgcaggac atcctggaaa aaacccataa tggcaaactg    180
tgcgatctgg atggcgtcaa accgctgatc ctgaaagatt gcagcgtggc gggttggctg    240
ctgggcaacc cgatgtgcga tgaatttatc aatgttccgg aatggagcta tattgtggaa    300
aaagcgaatc cgaccaacga tctgtgttat ccgggttcgt ttaacgatta cgaagaactg    360
aaacacctgc tgagccgtat taatcatttt gaaaaaatcc agattattcc gaaatcgagc    420
tggtcggacc acgaggcgag ctcgggcgtt tcctccgcct gcccgtatct gggtagcccg    480
agcttttttc gtaatgtggt ctggctgatc aaaaaaaatt ccacgtaccc gaccattaaa    540
aaaagctata acaacaccaa ccaggaagat ctgctggtgc tgtggggcat tcatcatccg    600
aacaatgaag aagaacagac ccgcctgtac cagaatccga ccacctatat tagcattggc    660
accagcaccc tgaatcagcg tctggttccg aaaattgcga cccgcagcaa agtgaacggc    720
cagtccggtc gtatggaatt tttttggacc attctgaaac cgaatgatgc catcaacttt    780
gaatccaatg gcaattttat cgcgccggaa tacgcgtata aaatcgtgaa aaaaggcgat    840
agcgccatta tgaaaagcga actggaatac tccaactgca atacgaaatg tcagacgccg    900
atgggcgcga tcaacagctc gatgccgttt cacaacatcc atccgctgac cattggcgag    960
tgtccgaaat atgtcaaaag cagccgcctg gtgctggcca ccggcctgcg caattcgccg   1020
cagcgtgaaa gccgtcgcaa aaaacgtggc ctgtttggcg cgattgcggg cttcattgaa   1080
```

```
ggcggctggc agggtatggt cgacggctgg tacggttatc atcatagcaa cgaacagggt    1140
agcggctatg cggcggataa agaatccacc cagaaagcca tcgatggtgt cacgaataaa    1200
gtgaatagca ttattgacaa aatgaacacc cagttcgagg cggtcggccg cgagtttaat    1260
aatctggaac gccgcattga aaatctgaat aaaaaaatgg aagatggctt tctggacgtt    1320
tggacctata acgcggaact gctggtcctg atggagaacg aacgcacgct ggactttcat    1380
gattccaacg tgaaaaatct gtacgataaa gttcgtctgc agctgcgcga caatgccaaa    1440
gaactgggca cggctgtttt cgagttttat cataaatgtg ataacgaatg catggaatcc    1500
attcgtaacg gtacctacaa ctatccgcag tatagcgaag aagcgcgcct gaaacgtgaa    1560
gagatttcgg gtgtgaaact ggaatccatt ggcacctatc agattctgtc catttatagc    1620
accgtcgcca gctccctggc cctggccatt atgattgcgg gcctgagcct gtggatgtgc    1680
tccaacggct ccctgcagtg tcgcatctgc atccccgggt caacttatgg gagccaggac    1740
tatcttaatc cattgattaa tgaaatcagc aaaatcattt cagctgcagg taatttggat    1800
gttaaggagg aaagatctgc cgcttcttta ttgcagttgt ccggtaatgc cagtgatttt    1860
tcatatggac ggaactcaat aactttgaca gcatcagcat aaaagcttga tc           1912

<210> SEQ ID NO 7
<211> LENGTH: 38
<212> TYPE: DNA
<213> ORGANISM: Unknown
<220> FEATURE:
<223> OTHER INFORMATION: PCR Primer

<400> SEQUENCE: 7
gatcgagctc ggcttaatta ttgcccagct tgcgctgg                             38

<210> SEQ ID NO 8
<211> LENGTH: 84
<212> TYPE: DNA
<213> ORGANISM: Unknown
<220> FEATURE:
<223> OTHER INFORMATION: PCR Primer

<400> SEQUENCE: 8
ccccgcatgc ggggctcgag ggggccatat aggccgggga tttaaatggg gcggccgcaa    60
aaaaaatcct ggcgcagggc cagg                                            84

<210> SEQ ID NO 9
<211> LENGTH: 79
<212> TYPE: DNA
<213> ORGANISM: Unknown
<220> FEATURE:
<223> OTHER INFORMATION: PCR Primer

<400> SEQUENCE: 9
ccccgcatgc ggggagatct ggggttaatt aaggggtcta gagggggcgg ccgcaggact    60
atatttaggg cgaaacagc                                                  79
```

```
<210> SEQ ID NO 10
<211> LENGTH: 36
<212> TYPE: DNA
<213> ORGANISM: Unknown
<220> FEATURE:
<223> OTHER INFORMATION: PCR Primer

<400> SEQUENCE: 10
gatcgtcgac gactaaacat gattccaaca atcacg                              36
```